(12) United States Patent
Gu et al.

(10) Patent No.: US 12,728,230 B2
(45) Date of Patent: Sep. 8, 2026

(54) VISUAL INTERFACE FOR MOTORIZED ENDOSCOPE CONTROL

(71) Applicants: BOSTON SCIENTIFIC SCIMED, INC., Maple Grove, MN (US); WORCESTER POLYTECHNIC INSTITUTE, Worcester, MA (US)

(72) Inventors: Anne Gu, Brighton, MA (US); Hannah R. Baez, Ann Arbor, MI (US); Avnish Sachar, Cambridge, MA (US); James Weldon, Newton, MA (US); Paris Marks Saint-Preux, Lowell, MA (US); Farid Tavakkolmoghaddam, Worcester, MA (US); Christopher J. Nycz, Holden, MA (US); Aditya Ambani, Brighton, MA (US)

(73) Assignees: BOSTON SCIENTIFIC SCIMED, INC., Maple Grove, MN (US); WORCESTER POLYTECHNIC INSTITUTE, Worcester, MA (US)

( * ) Notice: Subject to any disclaimer, the term of this patent is extended or adjusted under 35 U.S.C. 154(b) by 621 days.

(21) Appl. No.: 18/199,236

(22) Filed: May 18, 2023

(65) Prior Publication Data

US 2023/0372673 A1 Nov. 23, 2023

Related U.S. Application Data

(60) Provisional application No. 63/344,256, filed on May 20, 2022.

(51) Int. Cl.

*A61B 1/005* (2006.01)
*A61B 34/30* (2016.01)
*A61M 25/01* (2006.01)

(52) U.S. Cl.

CPC ....... *A61M 25/0136* (2013.01); *A61B 1/0052* (2013.01); *A61B 34/30* (2016.02); *A61B 2034/301* (2016.02)

(58) Field of Classification Search

CPC .............. A61B 1/0052; A61B 1/00045; A61B 2034/301; A61B 5/743; A61B 5/7435

See application file for complete search history.

(56) References Cited

U.S. PATENT DOCUMENTS 4,461,282 A 7/1984 Ouchi et al.
5,578,052 A 11/1996 Koros et al.
(Continued)

FOREIGN PATENT DOCUMENTS

DE 202010009234 U1 12/2011
JP H09492 A 1/1997
(Continued)

OTHER PUBLICATIONS

Asge, "Minimizing Occupational Hazards in Endoscopy: Personal Protective Equipment, Radiation Safety, and Ergonomics," Gastrointestinal Endoscopy Journal, vol. 72, No. 2, 9 pages, 227-235, 2010.

(Continued)

*Primary Examiner* — Anh T Nguyen
*Assistant Examiner* — Rynae E Boler
(74) *Attorney, Agent, or Firm* — Seager, Tufte & Wickhem LLP

(57) ABSTRACT

Steerable medical devices display systems including a handle and an elongate shaft extending distally from the handle to a distal tip, a motor control assembly including a motor control housing configured to detachably interface with the handle, a first deflection mechanism disposed within the handle, the first deflection mechanism being configured to deflect the distal tip in a first plane, and a work (Continued)

station in electronic communication with the motor control assembly, the work station including at least a display screen. The work station may be configured to display a dashboard including visual information of a position of the distal tip.

18 Claims, 11 Drawing Sheets

(56) References Cited

U.S. PATENT DOCUMENTS

| | | | | |
|---|---|---|---|---|
| 6,671,538 | B1 * | 12/2003 | Ehnholm | A61B 34/20 600/425 |
| 7,682,358 | B2 | 3/2010 | Gullickson et al. | |
| 7,686,816 | B2 | 3/2010 | Belef et al. | |
| 7,789,825 | B2 | 9/2010 | Nobis et al. | |
| 8,007,432 | B2 | 8/2011 | Vakharia et al. | |
| 8,010,180 | B2 | 8/2011 | Quaid et al. | |
| 8,337,397 | B2 | 12/2012 | Prisco et al. | |
| 8,808,168 | B2 | 8/2014 | Ettwein et al. | |
| 9,095,686 | B2 | 8/2015 | Zanne et al. | |
| 9,375,550 | B2 | 6/2016 | Tegg | |
| 9,402,604 | B2 | 8/2016 | Williams et al. | |
| 9,433,340 | B2 | 9/2016 | Jones et al. | |
| 10,299,684 | B2 | 5/2019 | Hendriks et al. | |
| 10,667,673 | B2 | 6/2020 | Su et al. | |
| 10,881,832 | B2 | 1/2021 | Chu | |
| 2001/0004676 | A1 | 6/2001 | Ouchi | |
| 2004/0267093 | A1 | 12/2004 | Miyagi et al. | |
| 2005/0267327 | A1 | 12/2005 | Iizuka et al. | |
| 2007/0225754 | A1 | 9/2007 | Measamer et al. | |
| 2007/0232856 | A1 | 10/2007 | Jeno et al. | |
| 2007/0270650 | A1 * | 11/2007 | Eno | A61B 1/0057 600/117 |
| 2010/0191224 | A1 | 7/2010 | Butcher | |
| 2010/0210908 | A1 | 8/2010 | Ashida et al. | |
| 2011/0275892 | A1 * | 11/2011 | Tanaka | A61B 1/00042 600/109 |
| 2014/0275763 | A1 | 9/2014 | King et al. | |
| 2014/0316203 | A1 | 10/2014 | Carroux et al. | |
| 2015/0335862 | A1 | 11/2015 | Selkee | |
| 2016/0270825 | A1 | 9/2016 | Wentz et al. | |
| 2016/0302644 | A1 * | 10/2016 | Umemoto | A61B 1/00148 |
| 2016/0324399 | A1 | 11/2016 | Banju et al. | |
| 2017/0143195 | A1 | 5/2017 | Yee et al. | |
| 2017/0215901 | A1 | 8/2017 | Harrah et al. | |
| 2019/0021707 | A1 | 1/2019 | Belsky et al. | |
| 2019/0029498 | A1 | 1/2019 | Mankowski et al. | |
| 2019/0208994 | A1 | 7/2019 | Davis | |
| 2019/0209810 | A1 | 7/2019 | Reid et al. | |
| 2019/0232027 | A1 | 8/2019 | Chu | |
| 2019/0313881 | A1 | 10/2019 | Francher | |
| 2019/0380562 | A1 | 12/2019 | Deuel et al. | |
| 2020/0078103 | A1 * | 3/2020 | Duindam | A61B 1/009 |
| 2020/0100647 | A1 | 4/2020 | Craig et al. | |
| 2020/0196834 | A1 | 6/2020 | Tah | |
| 2020/0345207 | A1 | 11/2020 | Nguyen et al. | |
| 2020/0352411 | A1 | 11/2020 | Tojo et al. | |
| 2021/0045619 | A1 | 2/2021 | Sauer | |
| 2021/0045626 | A1 | 2/2021 | Hsu et al. | |
| 2021/0085153 | A1 | 3/2021 | Chu et al. | |
| 2021/0186304 | A1 | 6/2021 | Joshi et al. | |
| 2021/0186306 | A1 | 6/2021 | Komuro | |
| 2021/0196399 | A1 | 7/2021 | Ayvali et al. | |
| 2022/0079418 | A1 * | 3/2022 | Ouyang | A61B 1/0016 |
| 2022/0160207 | A1 | 5/2022 | Nycz et al. | |
| 2022/0280021 | A1 | 9/2022 | Chu | |
| 2022/0304548 | A1 | 9/2022 | Chu | |
| 2022/0362518 | A1 | 11/2022 | Gu et al. | |
| 2025/0134603 | A1 * | 5/2025 | Ninni | A61B 90/361 |

FOREIGN PATENT DOCUMENTS

| | | | |
|---|---|---|---|
| WO | 2020049718 | A1 | 3/2020 |
| WO | 2020160522 | A1 | 8/2020 |
| WO | 2021127426 | A1 | 6/2021 |

OTHER PUBLICATIONS

Cho et al; "Evaluation of Performance Parameters of the Disposable Flexible Ureterorenoscope (LITHOVUE) in Patients with Renal Stones: A Prospective, Observational, Single-Arm, Multicenter Study," Scientific Reports, vol. 8:9795, 6 pages, Published online: Jun. 28, 2018.

Tian et al; "Cannulation Time is a More Accurate Measure of Cannulation Difficulty in Endoscopic Retrograde Cholangiopancreatography than the No. of Attempts," Gastroenterology Report, 1, pp. 193-197, Aug. 2013.

Tringali et al; "Endoscopic Retrograde Cholangiopancreatography: Indications, Patient Preparation and Complications," UpToDate®, Wolters Kluwer® 33 pages, Accessed Sep. 1, 2020.

International Search Report and Written Opinion dated Feb. 28, 2022 for International Application No. PCT/US2021/060305.

International Search Report and Written Opinion dated Jun. 10, 2022 for International Application No. PCT/US2022/018561.

Boston Scientific, Lithovue Empower™, Retrieval Deployment Device, Brochure, URO-554-002-AA, 4 pages, Jul. 2018.

International Search Report and Written Opinion dated Jun. 1, 2022 for International Application No. PCT/US2022/020951.

International Search Report and Written Opinion dated Aug. 8, 2022 for International Application No. PCT/US2022/028757.

Yung et al., "Muscoskeletal injuries in Gastrointestinal Endoscopists: A Systemic Review", Expert Review of Gastroenterology & Hepatology, 18 pages, 2017.

Cotton "Income and Outcome Metrics for the Objective Evaluationn of ERCP and Alternative Methods", Gastrointestinal Endoscopy, vol. 56, No. 6, (SUPPL) pp. S283-S290, 2002.

Freeman et al., "Prevention of Post-ERCP Pancreatitis: a Comprehensive Review", Gastrointestinal Endoscopy, vol. 59, No. 7, 20 pages, 2004.

Godard et al., "Unsupervised Monocular Depth Estimation with Left-Right Consistency", Proceedings of the IEEE Conference on Computer Vision and Pattern Recognition, pp. 270-279, 2017.

Klein et al., "Parallel Tracking and Mapping for Small AR Workspaces", Active Vision Laboratory Department of Engineering Science, University of Oxford, IEEE, 10 pages, 2017.

Kowalski et al., "Perceptions of Gastroenterology Fellows Regarding ERCP Competency and Training", Gastrointestinal Endoscopy, vol. 58, No. 3, pp. 345-349, 2003.

Petersen, "ERCP Outcomes: Defining the Operators, Experience, and Environments", An Editorial, Gastrointestinal Endoscopy, vol. 55, No. 7, pp. 953-958, 2002.

Vijayakumar et al., "Locally Weighted Projection Regression: An O(n) Algorithm for Incremental Real Time Learning in High Dimensional Space", Proceedings of Seventeenth International Conference on Machine Learning (ICML2000) pp. 1079-1086, 2000. (Abstract).

International Search Report and Written Opinion dated Aug. 3, 2023 for International Application No. PCT/US2023/022758.

* cited by examiner

VISUAL INTERFACE FOR MOTORIZED ENDOSCOPE CONTROL

CROSS-REFERENCE TO RELATED APPLICATIONS

This application claims the benefit of U.S. Prov. Pat. App. No. 63/344,256, filed May 20, 2022, titled VISUAL INTERFACE FOR MOTORIZED ENDOSCOPE CONTROL, which is incorporated herein by reference.

TECHNICAL FIELD

The disclosure is directed to a visual interface for motorized control of a medical device. More particularly, the disclosure is directed to a visual interface for enhanced control of a motorized medical device.

BACKGROUND

Medical devices, such as steerable/deflectable endoscopes and/or catheters, may be used to perform various diagnostic and/or treatment procedures. Different procedures may require different devices and/or different physical actions by the practitioner. Of the known medical devices, systems, and methods, each has certain advantages and disadvantages. There is an ongoing need to provide alternative medical devices and systems, including controls and interfaces for manipulating and maneuvering such medical devices.

SUMMARY

The disclosure is directed to several alternative visual interfaces for enhanced control of a motorized medical device, such as an endoscope.

In a first example, a steerable medical device and display system may comprise a handle and an elongate shaft extending distally from the handle to a distal tip, a motor control assembly including a motor control housing configured to detachably interface with the handle, a first deflection mechanism disposed within the handle, the first deflection mechanism being configured to deflect the distal tip in a first plane, and a work station in electronic communication with the motor control assembly. The work station may include at least a display screen. The work station may be configured to display a dashboard including visual information of a position of the distal tip.

Alternatively or additionally to any of the examples above, in another example, the visual information may include a location of the distal tip in two dimensions.

Alternatively or additionally to any of the examples above, in another example, the visual information may include a first bounding perimeter representing an available range of movement of the distal tip.

Alternatively or additionally to any of the examples above, in another example, the bounding perimeter may have a generally circular shape.

Alternatively or additionally to any of the examples above, in another example, the bounding perimeter may have a generally oval shape.

Alternatively or additionally to any of the examples above, in another example, the visual information may include two or more slide bars representing an available range of movement of the distal tip.

Alternatively or additionally to any of the examples above, in another example, at least one of the two or more slide bars may represent an available range of movement of the distal tip in a first direction and at least one of the two or more slide bars may represent an available range of movement of the distal tip in a second direction different from the first direction.

Alternatively or additionally to any of the examples above, in another example, the visual information may include two or more arcs representing an available range of movement of the distal tip.

Alternatively or additionally to any of the examples above, in another example, the system may further comprise a joystick control configured to operate at least a first motor to drive the first deflection mechanism.

Alternatively or additionally to any of the examples above, in another example, the visual information may include a location of the joystick control in two dimensions.

Alternatively or additionally to any of the examples above, in another example, the visual information may include a second bounding perimeter representing an available range of movement of the joystick control.

Alternatively or additionally to any of the examples above, in another example, the visual information may include a speed mode.

Alternatively or additionally to any of the examples above, in another example, the selected speed mode may include a display of two or more speed modes and a selected speed mode is highlighted.

Alternatively or additionally to any of the examples above, in another example, the visual information may include an indication of motor torque.

Alternatively or additionally to any of the examples above, in another example, the indication of motor torque may comprise a shaded bar.

In another example, a steerable medical device and display system may comprise a handle and an elongate shaft extending distally from the handle to a distal tip, a motor control assembly including a motor control housing configured to detachably interface with the handle, a first deflection mechanism disposed within the handle, the first deflection mechanism being configured to deflect the distal tip in a first plane, a motorized control interface configured to operate at least one motor disposed within the motor control housing, and a work station in electronic communication with the motor control assembly. The work station may include at least a display screen. The work station may be configured to display a dashboard including visual information of a position of the distal tip and a position of the motorized control interface.

Alternatively or additionally to any of the examples above, in another example, the position of the distal tip may be represented by a first icon and the position of the motorized control interface is represented by a second icon.

Alternatively or additionally to any of the examples above, in another example, the first icon may be configured to move on the display in response to movement of the distal tip.

Alternatively or additionally to any of the examples above, in another example, the second icon may be configured to move on the display in response to movement of the motorized control interface.

Alternatively or additionally to any of the examples above, in another example, the visual information may include a first bounding perimeter representing an available range of movement of the distal tip and a second bounding perimeter representing an available range of movement of motorized control interface.

Alternatively or additionally to any of the examples above, in another example, the first bounding perimeter and the second bounding perimeter may be concentric circles.

Alternatively or additionally to any of the examples above, in another example, a center point of the first and second bounding perimeters may be a neutral position for the distal tip and the motorized control interface.

In another example, a steerable medical device and display system may comprise a handle and an elongate shaft extending distally from the handle to a distal tip, a motor control assembly including a motor control housing configured to detachably interface with the handle, a first deflection mechanism disposed within the handle, the first deflection mechanism being configured to deflect the distal tip in a first plane, a motorized control interface configured to operate at least one motor disposed within the motor control housing, and a work station in electronic communication with the motor control assembly. The work station may include at least a display screen. The work station may be configured to display a dashboard including visual information of a position of the distal tip, a position of the motorized control interface, a selected speed mode and/or a motor torque.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

Embodiments of the disclosure may be more completely understood in consideration of the following detailed description in connection with the accompanying drawings, in which.

Figure 1:
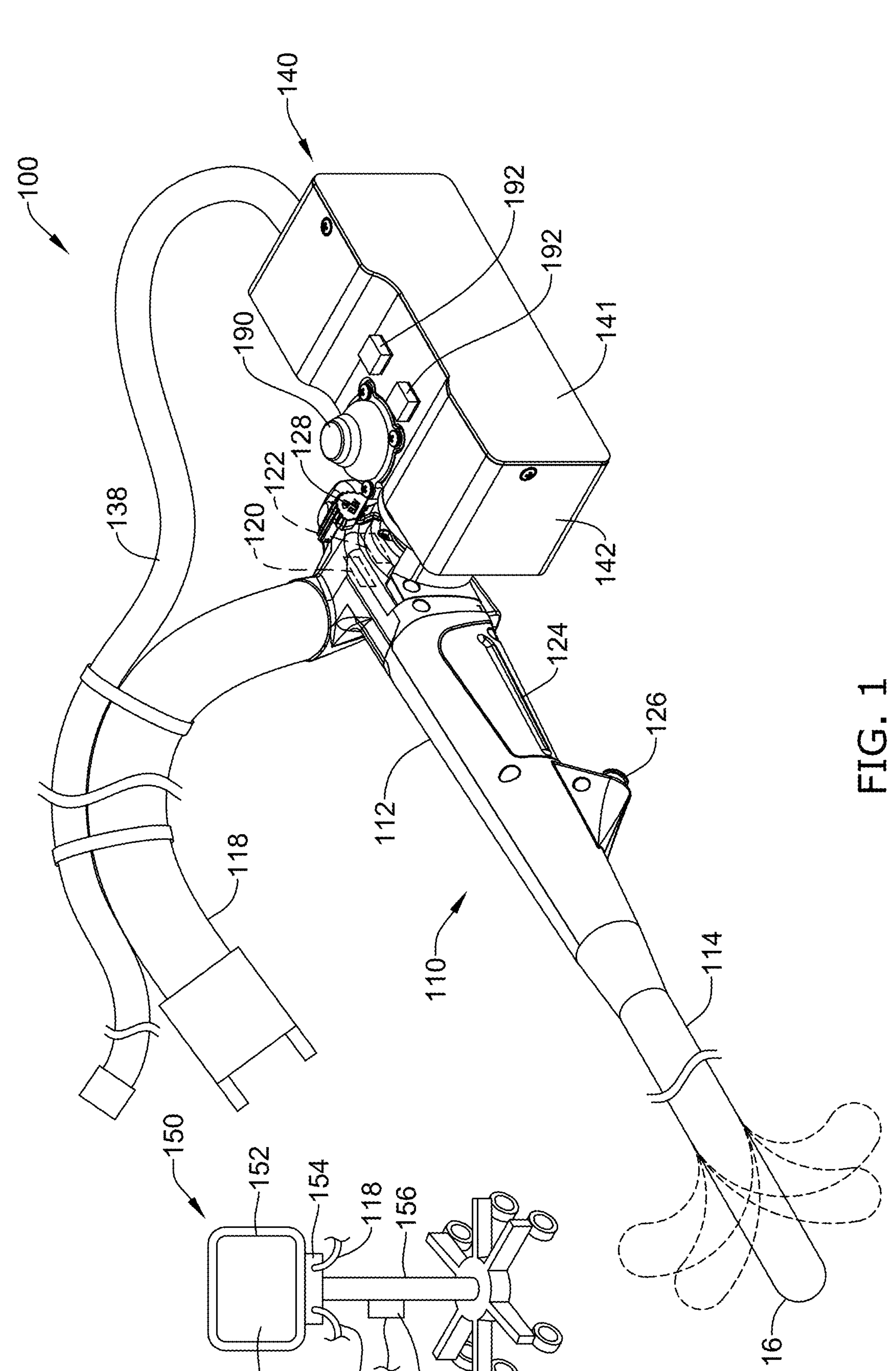
FIG. 1 illustrates selected aspects of a medical device, depicted as an endoscopic system.

While the embodiments of the present disclosure are amenable to various modifications and alternative forms, specifics thereof have been shown by way of example in the drawings and will be described in detail. It should be understood, however, that the intention is not to limit aspects of the present disclosure to the particular embodiments described. On the contrary, the intention is to cover all modifications, equivalents, and alternatives falling within the spirit and scope of the present disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claims. Those skilled in the art will recognize that the various elements described and/or shown may be arranged in various combinations and configurations without departing from the scope of the disclosure. The detailed description and drawings illustrate example embodiments. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the embodiments of the present disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Some medical/surgical procedures—for example: kidney stone management, ERCP (endoscopic retrograde cholangiopancreatography), pulmonary biopsy, colonoscopy, bladder mapping, cardiac mapping, cardiac valve replacement and/or repair, and others—may require navigation of an elongate shaft of a medical device through tortuous anatomy to position the elongate shaft, such as the distal tip of the elongate shaft, of the medical device(s) at a specific location and/or orientation. Some of these procedures may be long and/or may involve difficult physical actions that may lead to physician fatigue and/or musculoskeletal injury. In some medical/surgical procedures, the physician may be at risk of work-related strain due to repetitive motions, prolonged awkward posture(s), high forces, contact stress, and/or vibration. For example, some physicians may be at risk to develop De Quervain's tenosynovitis (swelling and pain at the base of the thumb), carpal tunnel syndrome, ganglion cysts, "trigger finger", and/or other conditions. In some instances, a physician's hand size may negatively affect his or her ability to control the medical device and/or perform medical/surgical procedures. Some medical devices may include features that may reduce and/or eliminate physician fatigue resulting from the procedure(s), may improve usability and/or ergonomics of the medical device for varying hand sizes, may provide more precision and/or more precise movements and stability when using the medical device, and may make using the medical device and/or performing certain procedures easier to learn. Such devices are described in commonly assigned U.S. Patent Application No. 63/187,988, filed May 13, 2021 and entitled MOTORIZED CONTROL FOR MEDICAL DEVICE, and U.S. patent application Ser. No. 17/741,887, filed May 11, 2022 and entitled MOTORIZED CONTROL FOR MEDICAL DEVICE; which applications are incorporated by reference herein.

In a traditional endoscope (e.g., not having motorized control), the knobs, which are used to control distal tip movement, provide physicians with haptic feedback to determine the distal tip's position as well as inherent force feedback to determine how much force the distal tip is applying to patient anatomy. Because a motorized endoscope replaces a manual control interface with a motorized control interface (e.g., a joystick or other input), the motorized endoscope may not have the haptic and force feedback which physicians are accustomed to. This lack of feedback may affect the physician's special awareness and sense of control when using the motorized endoscope. Additionally, this lack of feedback may frustrate physicians and negatively impact their willingness to adopt a motorized endoscope. Disclosed herein are systems and methods which incorporate a visual interface to mitigate the loss of haptic feedback and which may provide physicians with a greater sense of control.

FIG. 1 illustrates selected aspects of an exemplary medical device, depicted as an endoscopic system 100, which may include motorized control. In some embodiments, the endoscopic system 100 may include an endoscope 110. The endoscope 110 may be specific to a particular endoscopic procedure, such as, e.g., a ureteroscope, a cystoscope, a nephroscope, a duodenoscope, etc., or may be a general-purpose device suitable for a wide variety of procedures. In some embodiments, the endoscope 110 includes a handle 112 and an elongate shaft 114 extending distally from the handle 112 to a distal tip 116. The handle 112 includes a first deflection mechanism 120 configured to deflect and/or articulate the distal tip 116 of the elongate shaft 114 in a first plane and a second deflection mechanism 122 configured to deflect and/or articulate the distal tip 116 of the elongate shaft 114 in a second plane different from the first plane. In some embodiments, the first plane may be oriented at a non-zero angle to the second plane. In some embodiments, the first plane may be oriented perpendicular to the second plane. Other configurations are also contemplated. Although depicted as an endoscopic system 100 including an endoscope 110, it is noted and understood that features, components, and/or functionality described herein may be incorporated into another medical device, such as a steerable catheter or other medical device having one or more deflection mechanisms for controlling deflection and/or articulation of a distal tip of the elongate shaft of the medical device to facilitate navigation of the elongate shaft through the anatomy of a patient. Accordingly, the described components such as the handle, elongate shaft, deflection mechanisms, motor control assembly, and other components may be associated with another medical device having a deflectable/steerable distal tip of an elongate shaft, as desired.

In some embodiments, the first deflection mechanism 120 may include a first pulley or rotating member disposed within the handle 112 and operatively connected to the distal tip 116. In some embodiments, one or more first cables, wires, or other filaments may be engaged with and/or connected to the first pulley within the handle 112. For example, the one or more first cables, wires, or filaments may be engaged with and/or connected to the distal tip 116, such that tension applied to the one or more first cables, wires, or filaments by the first pulley deflects and/or articulates the distal tip 116 in the first plane. In some embodiments, the second deflection mechanism 122 may include a second pulley or rotating member disposed within the handle 112 and operatively connected to the distal tip 116. In some embodiments, one or more second cables, wires, or other filaments may be engaged with and/or connected to the second pulley within the handle 112. For example, the one or more second cables, wires, or filaments may be engaged with and/or connected to the distal tip 116, such that tension applied to the one or more second cables, wires, or filaments by the second pulley deflects and/or articulates the distal tip 116 in the second plane. Other configurations are also contemplated.

In some embodiments, the endoscopic system 100 may include a motor control assembly 140 including a motor control housing 142 configured to detachably interface with the handle 112 of the endoscope 110. In some embodiments, the motor control housing 142 may include a removable cover 141, where internal components of the motor control assembly 140 may be accessed after removing the removable cover 141. Additionally, in some embodiments, the motor control assembly 140 may include one or more internal covers (not explicitly shown) disposed within the motor control housing 142 that may protect certain components and/or groups of components from each other, contamination, etc. When so provided, the one or more internal covers may provide structural support for selected internal components. It shall be understood that the presence and/or use of all, some, or any of the one or more internal covers is optional and is not required.

The motor control assembly 140 may include at least one motor disposed within the motor control housing 142. In some embodiments, the at least one motor may include a first motor disposed within the motor control housing 142. In some embodiments, the at least one motor may include a second motor disposed within the motor control housing 142. In some embodiments, the at least one motor may include the first motor and the second motor disposed within the motor control housing 142. For each controlled degree of freedom of the distal tip 116, an individual motor may be added to the at least one motor.

The at least one motor may be electric and may be brushed or brushless DC motors. The at least one motor may provide the user partial force assistance for deflecting the distal tip 116, from 0% to 100% force assistance, thereby allowing for fully manual control, assisted control with reduced lever/knob force, or fully actuated control. Each motor may be attached to a rotary encoder which provides a relative position of said motor to the processor unit. In some embodiments, the at least one motor may be controlled by a central processing unit (CPU), a microprocessor, and/or a combination thereof. In some embodiments, additional inputs for the CPU, the microprocessor, and/or the combination thereof may include components of the user interface, tactile feedback electronics, etc.

In some embodiments, the motor control assembly 140 may include a user input mechanism or motorized control interface. For example, the user input mechanism may include one or more of a joystick control, a scroll wheel, a knob, a slider, a keypad, a touch screen interface or control, a voice interface or control, etc. In some embodiments, the motor control assembly 140 may include a joystick control 190 configured to operate the at least one motor disposed within the motor control housing 142. In some embodiments, the joystick control 190 may be configured to operate the first motor, the second motor, or both the first and the second motor. In some embodiments, the joystick control 190 may be configured to operate the first motor and the second motor simultaneously. In other embodiments, the joystick control 190 may be configured to operate the first motor and the second motor independently of each other. These are just some examples. Other configurations are also contemplated.

In some embodiments, the motor control assembly 140 may include a homing feature configured to return the distal tip 116 to a home position (e.g., to a straightened and/or non-deflected configuration) and/or a speed control feature configured to control speed and/or responsiveness of movement of the distal tip 116. In some embodiments, the homing feature and/or the speed control feature may each include an input mechanism. For example, the input mechanism may be one or more buttons, a voice interface and/or control, a gesture interface and/or control, or other suitable means of providing input to the motor control assembly 140 and/or the user interface.

In some embodiments, the motor control assembly 140 may include one or more buttons 192. In some embodiments, the one or more buttons 192 may include a first button configured to return the distal tip 116 to the home position, where activation of the first button automatically actuates the at least one motor to move the distal tip 116 to the home position. In some embodiments, the one or more buttons 192 may include a second button that is user configurable to retain a saved position or configuration, where activation of the second button automatically actuates the at least one motor to move the distal tip 116 to the saved position and/or configuration. Additional buttons and/or other configurations are also contemplated. Additionally, while the one or more buttons 192 are discussed herein by way of example, the motor control assembly 140 is not limited to the use of physical buttons and may include other input mechanisms.

In some embodiments, the motor control assembly 140 may include a self-homing feature and/or procedure. In one example, upon connecting the motor control assembly 140 to the handle 112, a homing program and/or algorithm is activated and/or run for the first motor and the second motor (where present) sequentially (e.g., the procedure is done on the first motor and then is done on the second motor). In some instances, the homing program and/or algorithm is automatically initiated when the motor control assembly 140 is connected to the handle 112. In other instances, the user may push a button, or otherwise manually initiate the homing program and/or algorithm after the motor control assembly 140 is connected to the handle 112. The first motor may start rotating in a first direction while the current is being monitored by the homing program and/or algorithm. Upon registering, encountering, and/or identifying a sudden increase in the amount of current drawn by the first motor, a location of an encoder is saved as a checkpoint for an upper limit or a lower limit. The first motor then starts turning in a second direction opposite the first direction and again upon registering, encountering, and/or identifying a sudden increase in the amount of current drawn by the first motor, the value of the encoder is saved as a second checkpoint for the other limit of the motion range for that axis and/or the first motor. After determining the upper limit and the lower limit of the first motor (and finding their corresponding values in terms of encoder values) the algorithm may divide the number of ticks between the upper limit and the lower limit by two. The corresponding encoder value would be the middle of the motion range or the home position for that axis and/or the first motor.

The same procedure is then repeated for the second motor, wherein the second motor may start rotating in the first direction while the current is being monitored by the homing program and/or algorithm. Upon registering, encountering, and/or identifying a sudden increase in the amount of current drawn by the second motor, a location of an encoder is saved as a checkpoint for an upper limit or a lower limit. The second motor then starts turning in the second direction opposite the first direction and again upon registering, encountering, and/or identifying a sudden increase in the amount of current drawn by the second motor, the value of the encoder is saved as a second checkpoint for the other limit of the motion range for that axis and/or the second motor. After determining the upper limit and the lower limit of the second motor (and finding their corresponding values in terms of encoder values) the algorithm may divide the number of ticks between the upper limit and the lower limit by two. The corresponding encoder value would be the middle of the motion range or the home position for that axis and/or the second motor.

In another example, the homing feature and/or procedure may be manually activated after engaging the motor control assembly 140 to the handle 112 of the endoscope 110. Other configurations are also contemplated.

In some embodiments, the joystick control 190 may be configured to control movement of the distal tip 116. In some embodiments, the joystick control 190 may be configured to control a speed at which the distal tip 116 moves and/or responsiveness of the joystick control 190. In some embodiments, the motor control assembly 140 may include a speed change control button. In some embodiments, the speed change control button may be built into and/or may be integrated into the joystick control 190. For example, in some embodiments, pressing axially on the joystick control 190 toward the motor control housing 142 may actuate the speed change control button. The speed change control feature and/or the speed change control button may actuate and/or cycle through a plurality of speed settings to permit at least some degree of customization over the speed and/or responsiveness of movement of the distal tip 116. In some embodiments, the plurality of speed settings may include at least a high speed setting which permits faster control and/or faster movement of the distal tip 116 and a low speed setting which permits finer control and/or slower movement of the distal tip 116. The plurality of speed settings may further include a medium speed setting and/or other speed settings (e.g., medium-high, medium-low, extra low, etc.).

In some embodiments, the motor control housing 142, the speed change control feature, the speed change control button, and/or the plurality of speed settings may be user customizable. For example, the user may be able to set speed mode(s), select and/or set desired speed(s), and/or set or save the speed mode(s) and/or desired speed(s). In some embodiments, the speed change control button may be depressed and held to set or save the speed mode(s) and/or desired speed(s). In some embodiments, the motor control housing 142 and/or the user interface may include additional buttons, a keypad, a scroll wheel, a dial, a touch interface, or other input mechanism for setting and/or adjusting the speed mode(s) and/or desired speed(s). These are only examples, and other configurations are also contemplated.

In some embodiments, the distal tip 116 may include a camera and may, for example, have deflection and/or articulation capabilities in one or more directions for viewing patient anatomy. In some embodiments, the endoscope 110 may be a duodenoscope such as an Exalt™ Model D scope. However, other medical devices, such as another endoscope (e.g., a ureteroscope, etc.) or related system, (e.g., Lithovue™ SpyScope™ DS, SpyGlass™ DS, etc.) may be used in addition to or in place of a duodenoscope and/or the endoscope 110. In some embodiments, the endoscope 110 may be configured to deliver fluid from a fluid management system to a treatment site via the elongate shaft 114. The elongate shaft 114 may include one or more working lumens for receiving a flow of fluid and/or other medical devices therethrough. In some embodiments, the endoscope 110 may be connected to the fluid management system via one or more supply line(s).

The handle 112 of the endoscope 110 may include a plurality of elements configured to facilitate the endoscopic procedure. In some embodiments, an umbilicus 118 extends from the handle 112 and is configured for attachment to an electronic device (not pictured) such as, for example, a computer system, a console, a microcontroller, etc. for providing power, analyzing endoscopic data, controlling the endoscopic intervention, and/or performing other functions. In some embodiments, the electronic device to which the umbilicus 118 is connected may have functionality for recognizing and exchanging data with other endoscopic accessories. The handle 112 may include a grip area 124 for the operating physician to grasp while performing the endoscopic procedure. In some embodiments, the handle 112 may include a side port 126 in communication with the one or more working lumens of the elongate shaft 114 and/or the endoscope 110.

In some embodiments, a motor control umbilicus 138 may extend from the motor control housing 142 and may be configured for attachment to an electronic device 150, which may be the same electronic device that the umbilicus 118 is attached to or may be a different electronic device as desired, for providing power, controlling endoscopic intervention and/or the motor control assembly, and/or other functions. In some embodiments, the motor control umbilicus 138 may be secured to the umbilicus 118. In some embodiments, the motor control umbilicus 138 may be releasably and/or removably secured to the umbilicus 118. In some embodiments, the motor control umbilicus 138 may be secured to the umbilicus 118 with a hook and loop closure device (e.g., Velcro™), tape, a wire tie, or other securement apparatus.

In some embodiments, the electronic device 150 may be a work station including a touch panel computer 152, an interface box 154 for receiving the wired connection(s) 118, 138, a cart 156, and a power supply 158 among other features. In some embodiments, the interface box 154 may be configured with a wired or wireless communication connection with the motor control assembly and/or endoscope 110. The touch panel computer 152 may include at least a display screen 160 and an image processor (not explicitly shown). In some embodiments, the workstation 150 may be a multi-use component (e.g., used for more than one procedure) while the endoscope 110 may be a single use device, although this is not required. It is contemplated that the electronic device 150 may take other forms, such as, but not limited to, a desktop computer, a laptop computer, a tablet, a handheld device, etc. Further, the electronic device 150 may include input means in addition to or in place of a touchscreen input, including, but not limited to, a keyboard, a mouse, a joystick, etc. As will be described in more detail herein, the display screen 160 may be configured to display a camera feed, a position of the distal dip 116, a speed of movement of the distal tip, etc.

In some embodiments, the handle 112 may include at least one communication interface for attaching accessory devices. In some embodiments, the handle 112 may include Universal Serial Bus type-C (USB-C) ports, Universal Serial Bus (USB) ports, ethernet ports, and/or other types of ports. In some embodiments, more, less, and/or other communication interfaces of various types, including, for example, custom interfaces, may be used. In some embodiments, the handle 112 has only one communication interface but may be connectable to e.g. a USB hub with multiple ports for connecting multiple accessories. The at least one communication interface may provide power to the accessory device(s) in addition to exchanging data therewith. Thus, the accessory device(s) need not have separate cables running to a connected electronic device or a battery that adds additional weight to the handle 112. In some embodiments, the accessory device(s) may be uniquely associated with the endoscope 110 and recognized by the electronic device through "plug and play" functionality without any user setup required.

In some embodiments, the endoscope 110 may include one or more sensors proximate the distal tip 116 and/or the distal end of the elongate shaft 114. For example, the endoscope 110 may include a pressure sensor at the distal tip 116 of the elongate shaft 114 to measure intracavity pressure within the treatment site. The endoscope 110 may also include other sensors such as, for example, a temperature sensor, a Fiber Bragg grating optical fiber to detect stresses, and/or an antenna or electromagnetic sensor (e.g., a position sensor). In some embodiments, the distal tip 116 and/or the distal end of the endoscope 110 may also include at least one camera to provide a visual feed to the user on the display screen of the touch panel computer. In another embodiment, the endoscope 110 may include two cameras having different communications requirements or protocols so that different information may be relayed to the user by each camera. When so provided, the user may switch back and forth between the cameras at will through the touch screen interface and/or the touch panel computer. While not explicitly shown, the elongate shaft 114 may include one or more working lumens for receiving the fluid and/or other medical devices. In some embodiments, the distal tip 116 may include an elevator configured to manipulate a guidewire, a tool, a medical instrument, etc. extending through the elongate shaft 114. The handle 112 may include an elevator control 128 operably connected to the elevator. In some embodiments, the at least one motor may include a motor configured to control and/or power movement of the elevator. In some embodiments, an elevator motor may be disposed within the handle 112 of the endoscope 110.

In some embodiments, the location of the distal tip 116 and/or the distal end of the elongate shaft 114 may be tracked during use. For example, a mapping and navigation system may include an operating table (or other procedural or examination table or chair, etc.) configured to act or function as an electromagnetic generator to generate a magnetic field of a known geometry. Alternatively, or additionally, an electromagnetic generator separate from the operating table may be provided. The operating table and/or the electromagnetic generator may be coupled to a control unit which may include among other features, a processor, a memory, a display, and an input means. A position sensor (e.g., the electromagnetic sensor, etc.) or antenna, may be incorporated into the distal tip 116 and/or the distal end of the elongate shaft 114 of the endoscope 110. The position sensor may be configured for use in sensing a location of the position sensor in the magnetic field of the mapping and navigation system. In some embodiments, the position sensor may be electronically coupled to the workstation 150. When the position sensor is in the magnetic field, the location of the position sensor can be mathematically determined relative to the electromagnetic field source (e.g., the operating table and/or the electromagnetic generator). The workstation and the control unit may communicate to determine the position of the position sensor relative to the patient.

Figure 2:
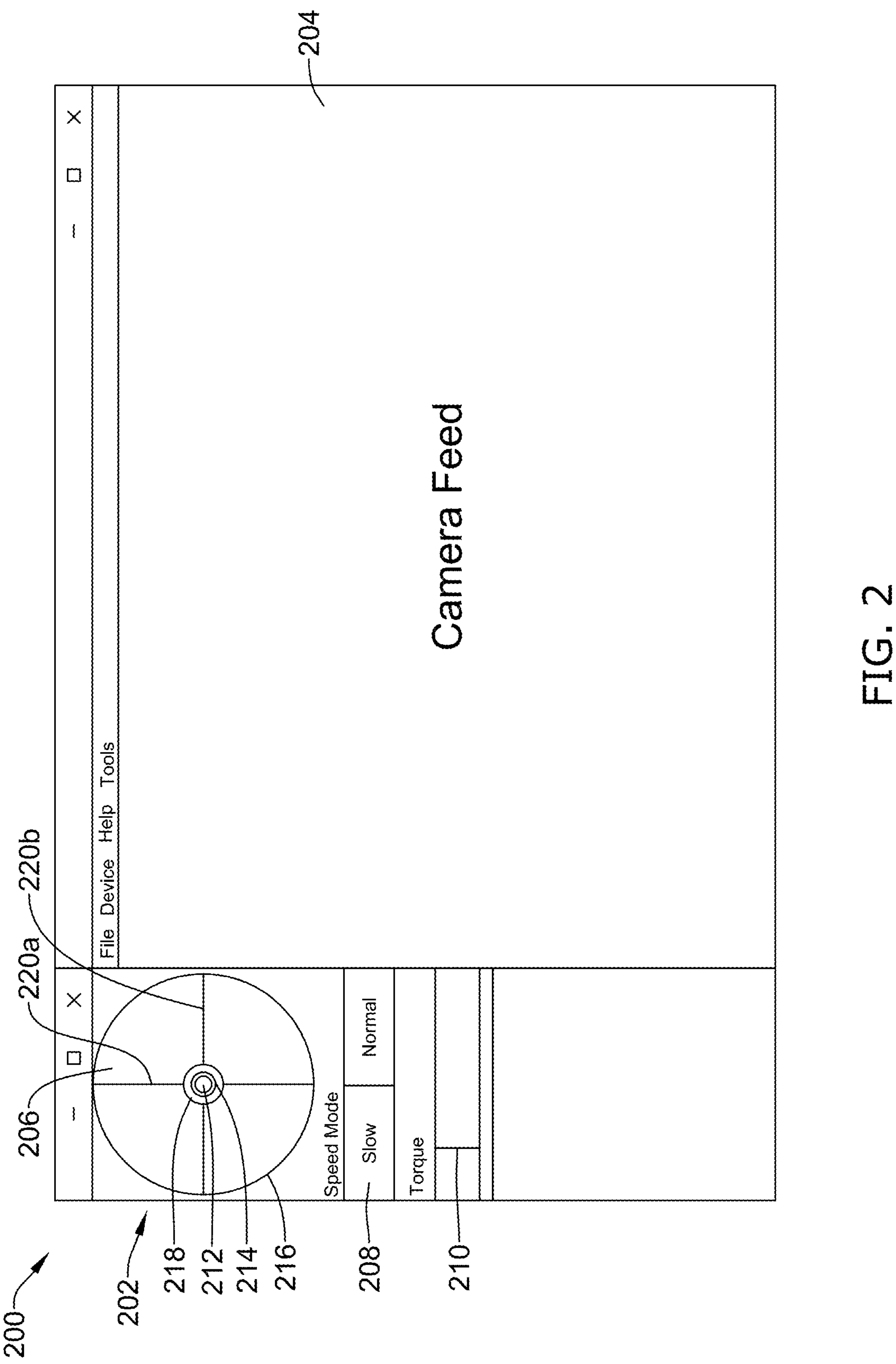
FIG. 2 is a schematic view of an illustrative graphical user interface.

FIG. 2 is a schematic view of an illustrative graphical user interface (GUI) 200 for providing feedback to a physician. The work station 150 may be configured to display the GUI 200 on the display screen 160 thereof. The visual interface 200 may be displayed, for example, on the touch panel computer 152, or other display device, as desired. The visual interface 200 may provide a first dashboard or window 202 to the physician and include visual information regarding the distal tip position with respect to the scope, distal tip speed, and an indication of the amount of force exerted on the distal tip 116. In some cases, the distal tip position with respect to the scope may be provided in a first region 206 of the window 202, the distal tip speed provided in a second region 208 of the window, and the indication of the amount of force exerted on the distal tip in a third region 210 of the window 202. In other embodiments, the information may be displayed in more than one window. For example, while not explicitly shown, the first, second, and third regions 206, 208, 210 may each be a separate window. It is further contemplated that the endoscope's camera feed may be displayed in an additional window 204.

The distal tip position relative to the longitudinal axis of the elongate shaft 114 may be represented in two dimensions (2-D), as shown in the first region 206. However, the distal tip position may be represented in three dimensions (3-D) with the addition of a sensor in the distal tip 116. In FIG. 2, the location of the distal tip 116 may be represented by a first shape or icon 212. In the illustrated embodiment, the first icon 212 is a circle; however, other geometric shapes or images may be used as desired. In some cases, the first icon 212 may have a first color selected such that the position of the distal tip 116 is easily identified. It is further contemplated that the location of the joystick 190 may be represented by a second shape or icon 214. In the illustrated embodiment, the second icon 214 is a circle; however, other geometric shapes or images may be used as desired. In some cases, the second icon 214 may have a second color different from the first color of the first icon 212 selected and/or the first icon 212 may be a different size than the second icon 214 such that the position of the joystick 190 is easily identified.

The first region 206 may further include bounding perimeters 216, 218 representative of the maximum movement (e.g., deflection) of the distal tip 116 and the joystick 190, respectively. The bounding perimeters 216, 218 may be concentric circles with the focus or center point of the perimeters 216, 218 representing a neutral position for both the distal tip 116 and the joystick 190. The distance from the centroid or center of the circle to the perimeter 216 may be representative of the amount or range of deflection allowed in a given direction. While the bounding perimeters 216, 218 are illustrated as being circular in shape, the bounding perimeters 216, 218 are representative of the degree or distance of movement of the component or the available range of motion in a given direction. For example, if the distal tip 116 is configured to deflect to a greater extent in one direction than another, the bounding perimeter 216 may have an oblong or oval shape with the distance from the centroid of the shape to a perimeter of the shape representative of the amount or range of deflection allowed in a given direction. This is just one example. The bounding perimeters 216, 218 may take other shapes, as desired. In some embodiments, the bounding perimeters 216, 218 may have a third color different from the first and second colors. The first region 206 may further include cross-hairs **220*a*, 220*b* (collectively, 220). The first cross-hair 220*a* may represent movement in a first direction (e.g., up/down) by a first motor and the second cross-hair 220*b* may represent movement in a second direction (e.g., left/right) by a second motor. The cross-hairs 220 may extend generally orthogonal to one another and may be used to help determine a position of the distal tip 116. In some embodiments, the cross-hairs 220 may have a same color as the bounding perimeters 216, 218, although this is not required. The cross-hairs 220** may have a fourth color different from the first, second, and third colors, if so desired.

Figure 3:
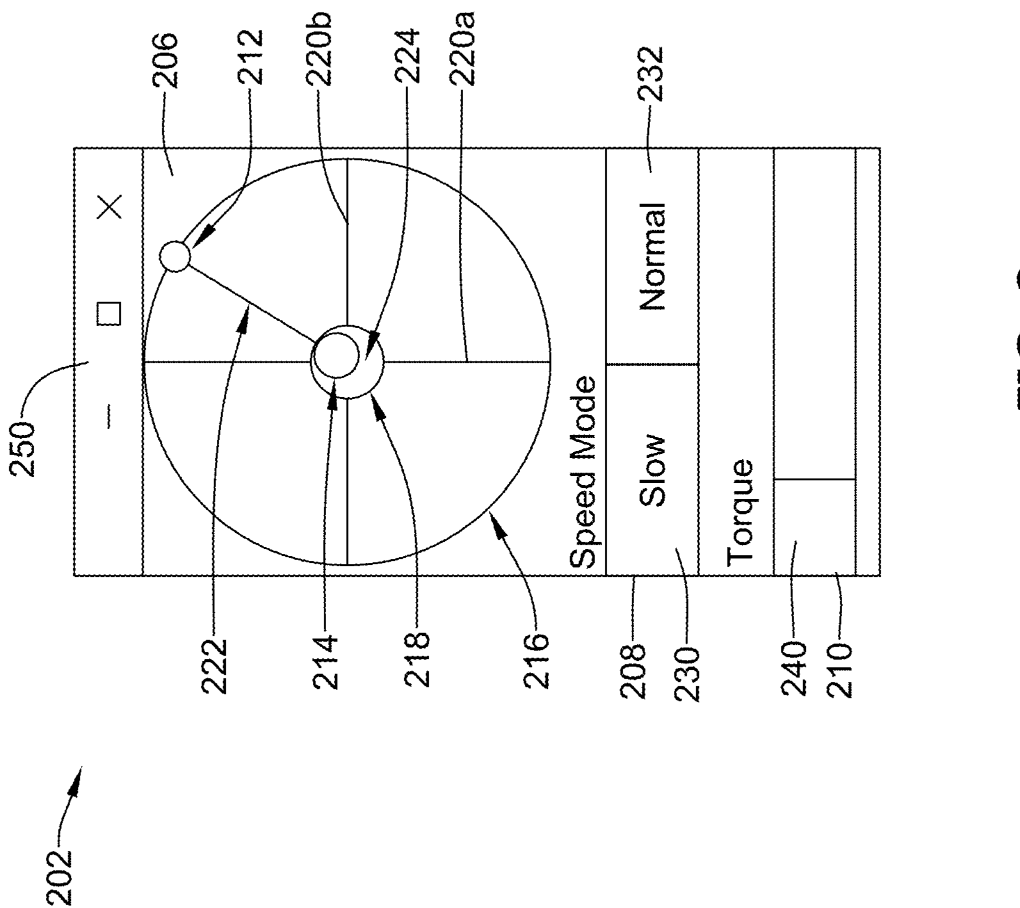
FIG. 3 is another schematic view of a portion of the illustrative graphical user interface of FIG. 2.

When the distal tip 116 is in the neutral position and the joystick 190 is unmoved, both the first and second icons 212, 214 representing the distal tip 116 and the joystick 190, respectively, are shown to be at the origin of the cross-hairs 220, as shown in FIG. 2. Referring additionally to FIG. 3, which illustrates the first window 202 with the distal tip 116 and the joystick 190 in a deflected configuration, as the user jogs or moves the joystick 190, the location of the joystick 190 is shown to the user using the second icon 214. As the distal tip 116 moves, so does the first icon 212. The distance of the distal tip 116 from the neutral position (e.g., extent of deflection of the distal tip 116 from the neutral position) may be indicated by a line 222 extending between the origin and the first icon 212, as shown in FIG. 3. The line 222 may be the same color as the first icon 212, although this is not required.

When the motorized endoscope system 100 is turned on, the calibration of the distal tip 116 with respect to the joystick 190 and the dashboard 202 initiates through a homing procedure, which may be done in addition to, simultaneously with, or in place of the homing procedure of the motors. During the homing procedure, the distal tip 116 is automatically moved to the extreme or maximal "up" position followed by the extreme or maximal "down" position and the respective encoder values for these positions are stored in system memory. The same process is done for the extreme or maximal "left" and extreme or maximal "right" positions of the distal tip 116, respectively. These stored encoder values are the maximum and minimum positions of the system in the X and Y axes, respectively. This positional information may be then used to calculate the encoder values for the neutral or home position 224 for the distal tip 116. For the dashboard 202, this neutral/home position 224 is signified by the center of the bounding perimeters 216, 218 or the intersection of the cross-hairs 220, as shown in FIG. 3. Further, the maximum and minimum encoder values for the two axes may be used to give a scaled radius for the bounding perimeters 216, 218. For the dashboard 202, the encoder values may also be scaled to accurately represent them within the circle. Thus, each point within the area of the circle represents a set of encoder values for the two motors which helps determine the location of the distal tip in 2D space (projected from the actual 3D space).

Figure 4A:
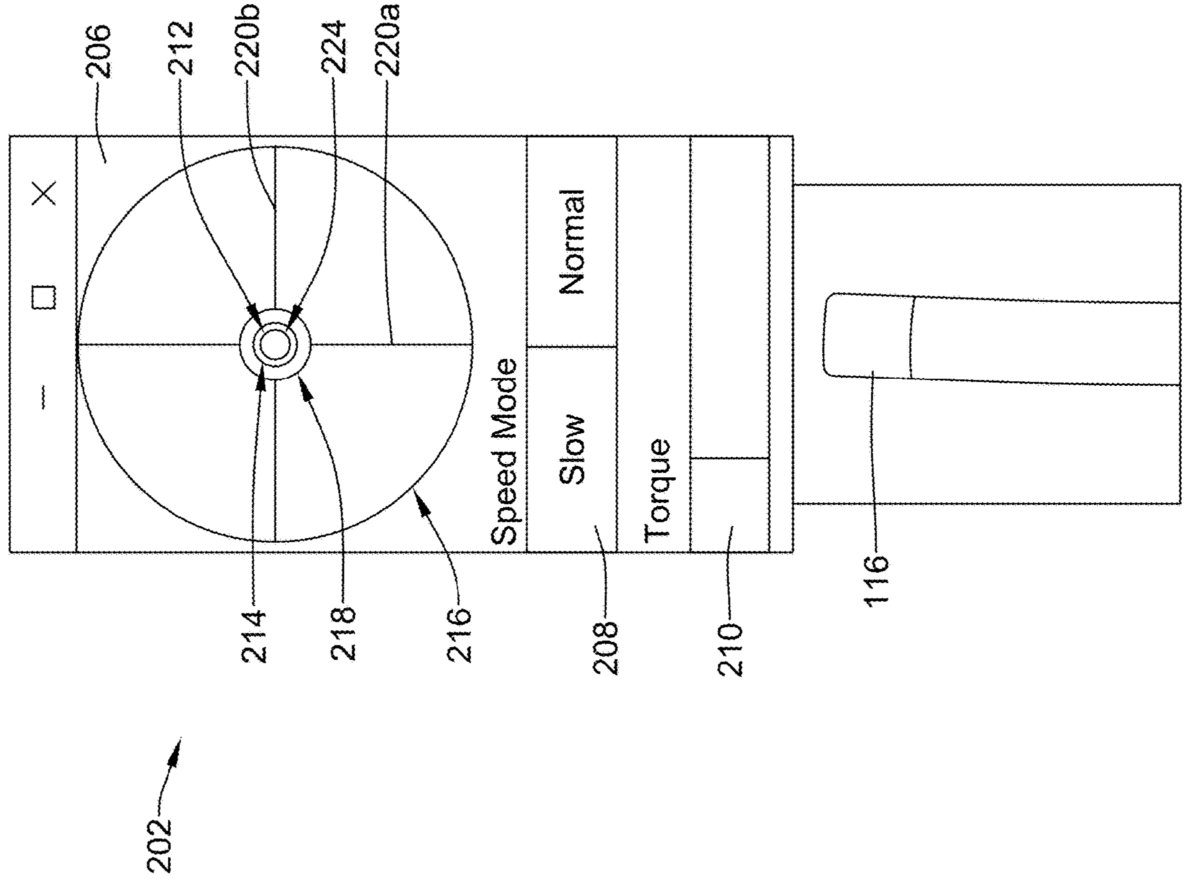
FIGS. 4A-4D illustrate how the graphical user interface of FIG. 2 reacts to a moving component of the endoscopic system.
Figure 4B:
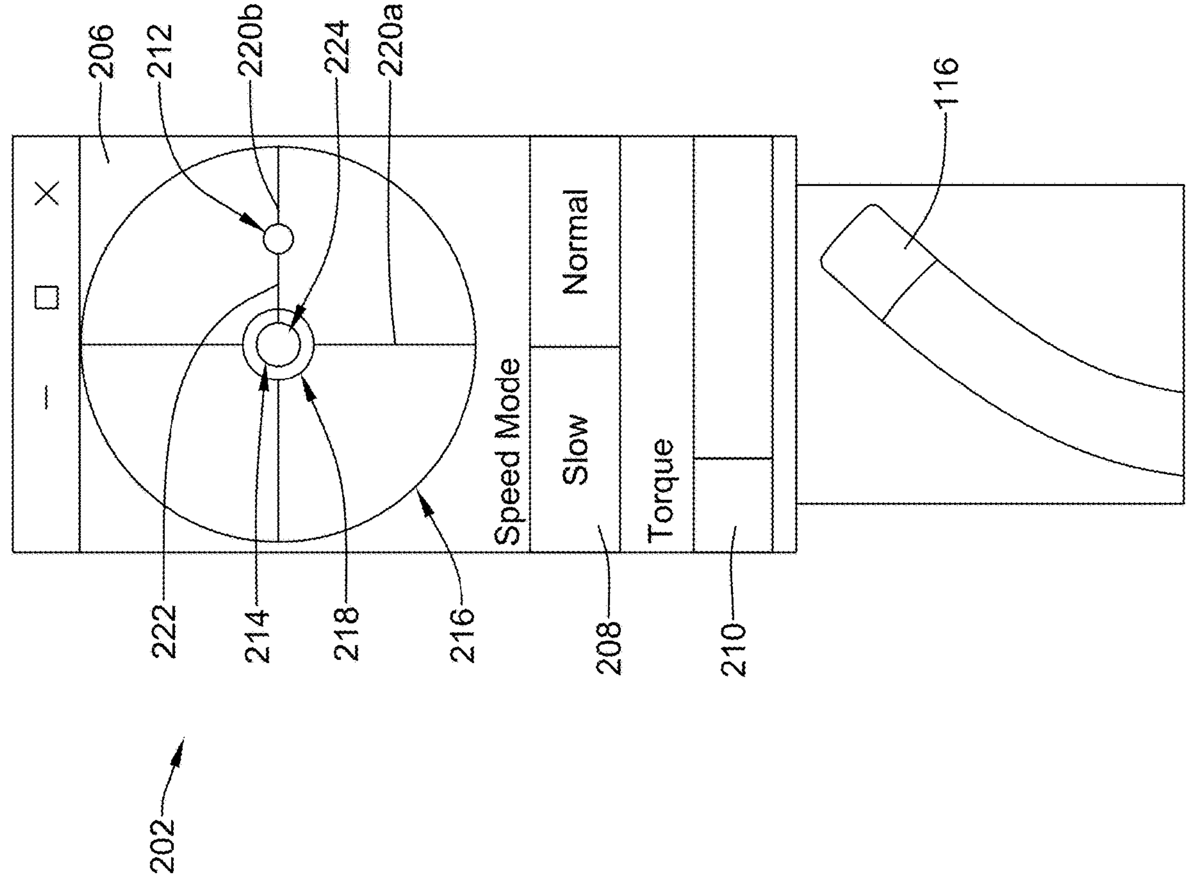
Figure 4C:
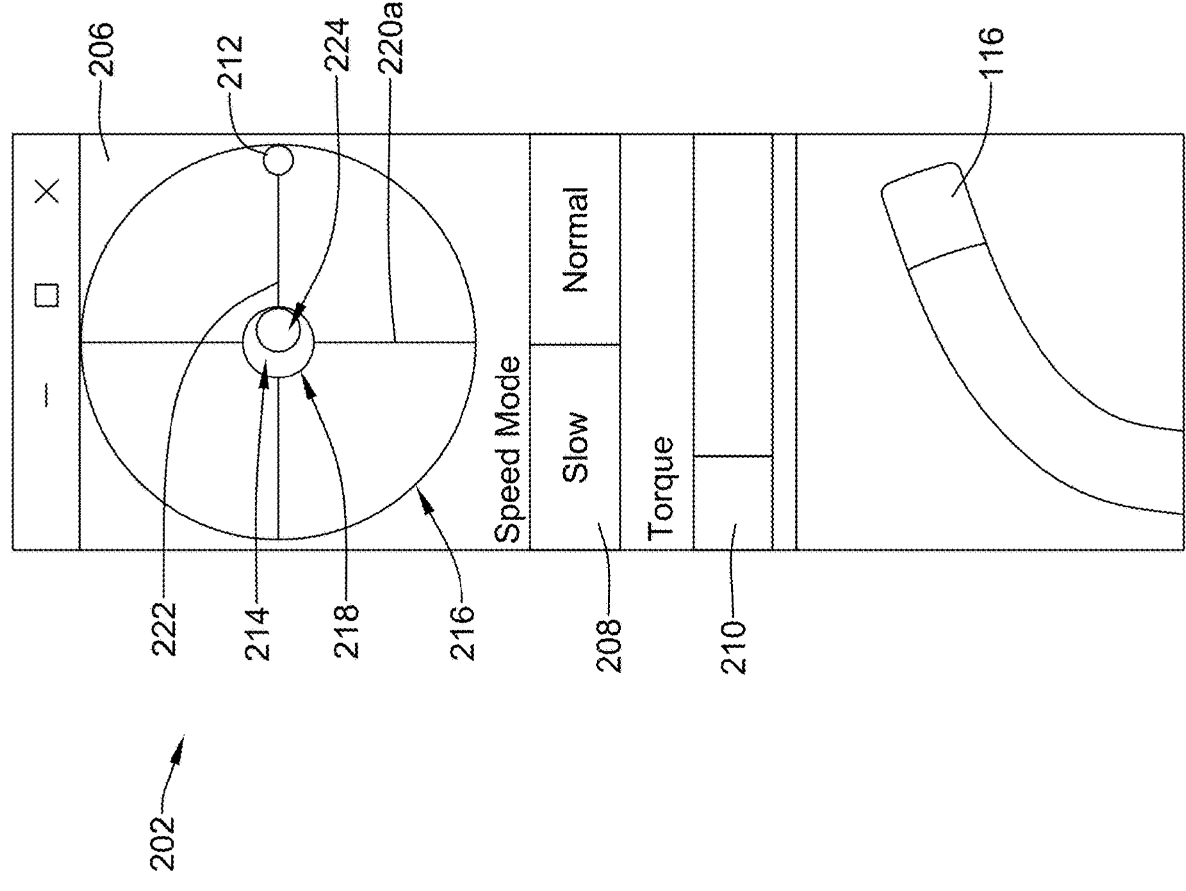
Figure 4D:
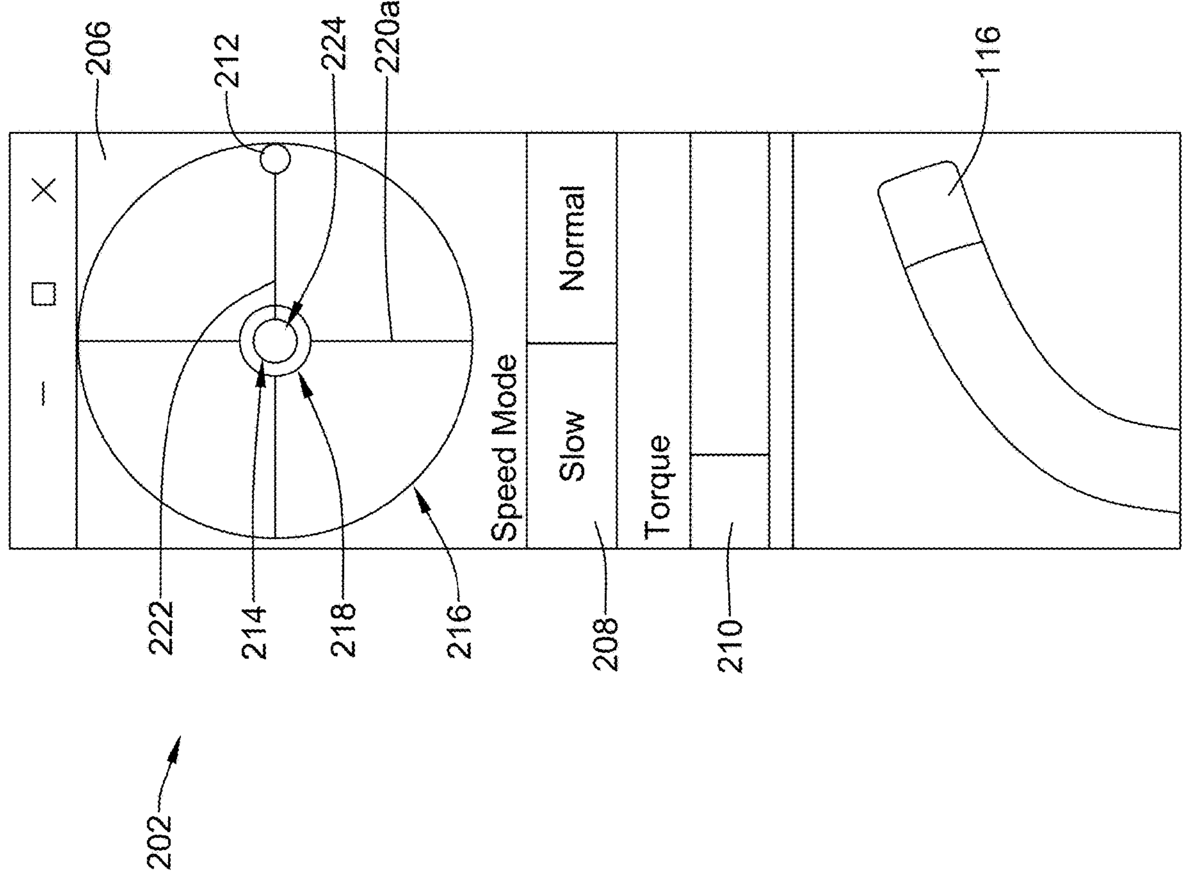

FIGS. 4A-4C illustrate how the dashboard 202 reacts to the user moving the distal tip 116 from the neutral position (FIG. 4A) to the extreme right position (FIG. 4C). FIG. 4A illustrates the distal tip 116 in a neutral or home position. As can be seen in FIG. 4A, the dashboard 202 correspondingly shows the first icon 212 (tip position) and second icon 214 (joystick position) as centered at the neutral/home position 224. FIG. 4B illustrates a first intermediate position of the distal tip 116 between the neutral position and an extreme right position. As can be seen in FIG. 4B, the dashboard 202 correspondingly shows the first icon 212 (tip position) and second icon 214 (joystick position) moved to the right of the neutral/home position 224 Further, the dashboard 202 also includes the line 222 indicative of the distance the distal tip 116 has moved from center (e.g., the amount of deflection of the distal tip 116 from its neutral or home position). FIG. 4C illustrates the distal tip 116 in an extreme right position. As can be seen in FIG. 4C, the dashboard 202 correspondingly shows the first icon 212 (tip position) and second icon 214 (joystick position) moved to the right extreme of the bounding perimeters 216, 218 Further, the dashboard 202 also includes the line 222 indicative of the distance the distal tip 116 has moved from center (e.g., the amount of deflection of the distal tip 116 from its neutral or home position), which is longer than the line 222 of FIG. 4B. Once the distal tip 116 is jogged or moved all the way to the right, as shown in FIG. 4C, the user may release the joystick 190. FIG. 4D illustrates the dashboard 202 once the user releases the joystick 190 after the distal tip 116 is in the desired position (e.g., in the illustrated embodiment, to the extreme right). The distal tip 116 may be configured to maintain the deflected configuration once the joystick 190 has been released until the joystick 190 is actuated to move the distal tip 116 into a different configuration. The second icon 214 (joystick position) has returned to the neutral/home position 224, as the user is no longer actuating the joystick (e.g., it has been released) while the first icon 212 (tip position) remains at the bounding perimeter 216. While FIGS. 4A-4D are shown and described as the distal tip 116 moving to the extreme right configuration, it should be understood the distal tip 116 may be moved in any direction or combination of directions allowed by the one or more motors.

As described above, the system 100 may allow the user to select and move between two or more speeds at which the distal tip 116 moves and/or a responsiveness of the joystick control 190. Returning to FIG. 3, the dashboard 202 may also be configured to display a selected speed mode, as shown at region 208. For example, the dashboard 202 may illustrate the various speed modes as icons or panels 230, 232. The selected speed mode may be highlighted or illuminated to indicate the selection. Alternatively, or additionally, when a user selects a speed mode, the speed mode panel 208 may be displayed and then minimized after a predetermined length of time (e.g., a few seconds, a minute, etc.). For instance, in some instances when a user selects a speed mode, the selected speed mode may be displayed in enlarged text on the display for a predetermined length of time (e.g., a few seconds, a minute, etc.) and then the size, location, etc. of the text of the selected speed may be changed, such as reduced in size, moved to another location on the display, or removed from the display, if desired. In FIG. 3, the normal speed 232 has been selected and is illuminated while the slow speed 230 is shaded. It is contemplated that the selected speed may be highlighted in a same color as the first icon 212 (tip position), although this is not required. Further, while the dashboard 202 is illustrated as including two speeds and two corresponding panels 230, 232, the dashboard 202 may include any number of buttons to correlate to the number of speed options. For example, a "high" speed panel may be provided in addition to or in place of the "slow" panel 230 or "normal" panel 232.

Additionally, the amount of motor torque may also be displayed on the dashboard 202 at the third region 210. The amount of force feedback on the distal tip 116 that the physician would otherwise feel when navigating through the patient's autonomy can be calculated by measuring motor current against motor torque. This may be displayed to the physician as a shaded bar 240 that increases in size with an increase in force. It is contemplated that the shaded bar 240 may be a same color as the first icon 212 (tip position), although this is not required. A maximum torque may extend an entire width of the dashboard 202 or to an identified maximum torque, as desired. Once the shaded bar 240 reaches the maximum force (e.g., the motor torque value at which the motor current reaches the pre-determined permissible limit), the user may be prohibited from increasing the force. This maximum force could be calculated by measuring the motor current against the motor torque through testing. In some cases, the user or developer may determine the maximum force. While the torque is illustrated as a shaded bar 240, it is contemplated that the torque may be displayed in other manners as well. Alternatively, or additionally, if a pressure sensor is present at the distal tip 116, the pressure measured at the pressure sensor may be used to show the amount of force feedback at the distal tip 116. The pressure may be displayed in addition to the motor torque or in place of the motor torque, as desired.

The dashboard 202 may include additional features. For example, the user may have the ability to manipulate the size and location of the dashboard 202 on the screen and the ability to select which dashboard features are displayed at a control bar 250. In some embodiments, the user may choose to display one of or a combination of two or more of: (1) distal tip location 206, (2) speed mode 208, and/or (3) force feedback (e.g., torque) 210. It is further contemplated that the user may selected a display style for any of the (1) distal tip location 206, (2) speed mode 208, and/or (3) force feedback (e.g., torque) 210. For example, alternative display configurations are described below. In some cases, the user can choose to minimize, expand, or close the dashboard 202. Manipulating the dashboard 202 could be accomplished by joystick input, or other input, or by using a touchscreen in order to directly manipulate on the video display screen.

Figure 5:
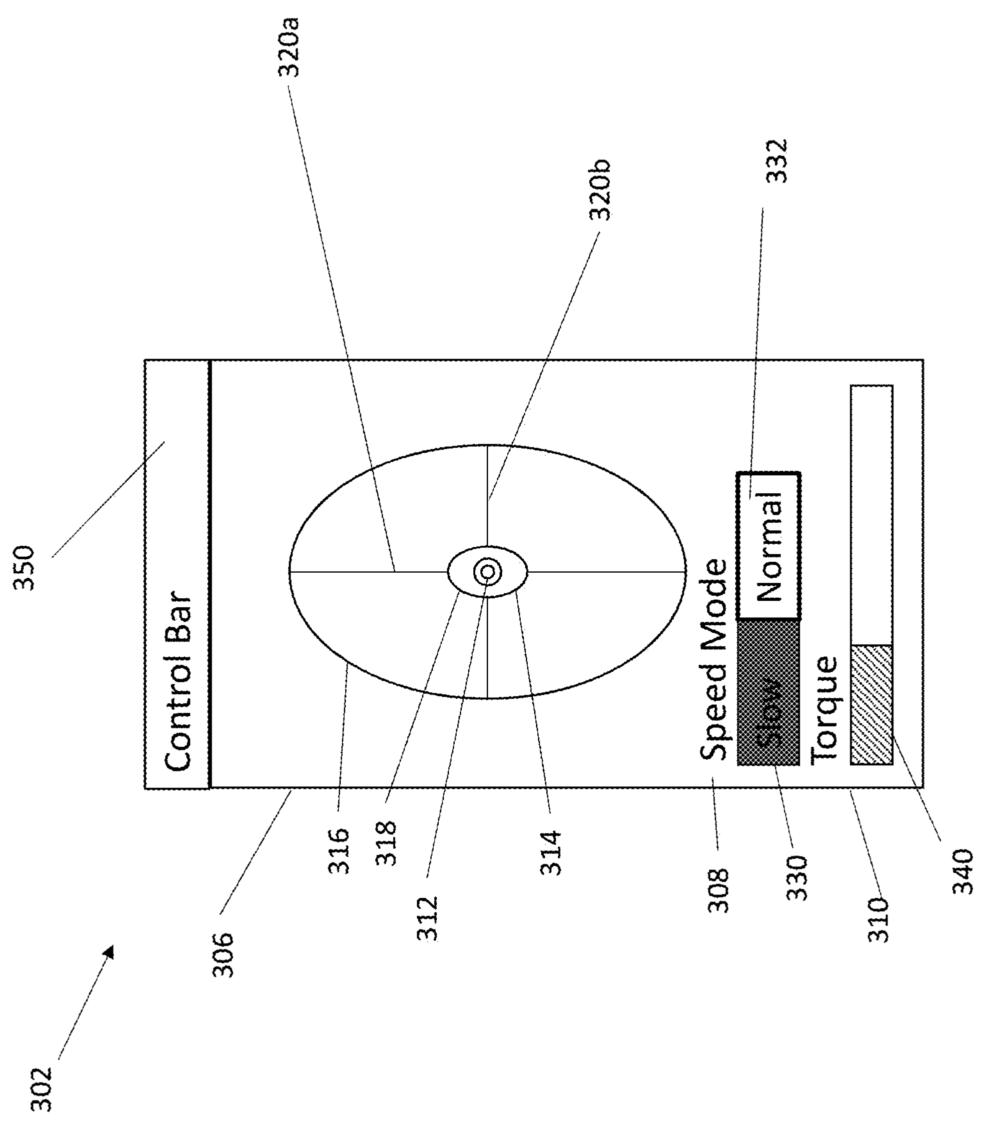
FIGS. 5-8 are schematic views of alternative configurations for the graphical user interface.

FIG. 5 is a schematic view of an illustrative graphical user interface (GUI) 302 or dashboard for providing feedback to a physician. The dashboard 302 may be displayed, for example, on the touch panel computer 152, or other display device, as desired. The dashboard or window 302 may be visible to the physician and include visual information regarding the distal tip position with respect to the scope, distal tip speed, and an indication of the amount of force exerted on the distal tip 116. In some cases, the distal tip position with respect to the scope may be provided in a first region 306 of the window 302, the distal tip speed provided in a second region 308 of the window, and the indication of the amount of force exerted on the distal tip in a third region 310 of the window 302. In other embodiments, the information may be displayed in more than one window. For example, while not explicitly shown, the first, second, and third regions 306, 308, 310 may each be a separate window. It is further contemplated that the endoscope's camera feed may be displayed in an additional window (not explicitly shown).

The distal tip position relative to the longitudinal axis of the elongate shaft 114 may be represented in two dimensions (2-D), as shown in the first region 306. However, the distal tip position may be represented in three dimensions (3-D) with the addition of a sensor in the distal tip 116. In FIG. 5, the location of the distal tip 116 may be represented by a first shape or icon 312. In the illustrated embodiment, the first icon 312 is a circle; however, other geometric shapes or images may be used as desired. In some cases, the first icon 312 may have a first color selected such that the position of the distal tip 116 is easily identified. It is further contemplated that the location of the joystick 190 may be represented by a second shape or icon 314. In the illustrated embodiment, the second icon 314 is a circle; however, other geometric shapes or images may be used as desired. In some cases, the second icon 314 may have a second color different from the first color of the first icon 312 selected such that the position of the joystick 190 is easily identified.

The first region 306 may further include bounding perimeters 316, 318 representative of the maximum movement of the distal tip 116 and the joystick 190, respectively. In FIG. 5, the bounding perimeters 316, 318 have a generally oval shape. The bounding perimeters 316, 318 reflect a range of motion (e.g., amount of deflection) of the distal tip 116 that is greater in the up/down direction than the left/right direction. It should be understood that if the range of motion were greater in the left/right direction, the major axis of the bounding perimeters 316, 318 would extend left to right as opposed to up/down as shown in FIG. 5. The distance from the centroid or center of the oval to the perimeter 316 may be representative of the amount of deflection allowed in a given direction. The bounding perimeters 316, 318 may take other shapes, as desired. In some embodiments, the bounding perimeters 316, 318 may have a third color different from the first and second colors. The first region 306 may further include cross-hairs 320*a*, 320*b* (collectively, 320). The first cross-hair 320*a* may represent movement in a first direction (e.g., up/down) by a first motor and the second cross-hair 320*b* may represent movement in a second direction (e.g., left/right) by a second motor. The cross-hairs 320 may extend generally orthogonal to one another and may be used to help determine a position of the distal tip 116. In some embodiments, the cross-hairs 320 may have a same color as the bounding perimeters 316, 318, although this is not required. The cross-hairs 320 may have a fourth color different from the first, second, and third colors, if so desired.

When the distal tip 116 is in the neutral position and the joystick 190 is unmoved, both the first and second icons 312, 314 representing the distal tip 116 and the joystick 190, respectively, are shown to be at the origin of the cross-hairs 320, as shown in FIG. 5. As the user jogs or moves the joystick 190, the location of the joystick 190 is shown to the user using the second icon 314. As the distal tip 116 moves, so does the first icon 312. The distance of the distal tip 116 from the neutral position (e.g., extent of deflection of the distal tip 116 from the neutral position) may be indicated by a line (not explicitly shown) extending between the origin and the first icon 312. The line may be the same color as the first icon 312, although this is not required. It is contemplated that the first region 306 may display the location of the distal tip 116 and/or the joystick 190 in a manner similar to that described with respect to FIGS. 4A-4D.

When the motorized endoscope system 100 is turned on, the calibration of the distal tip 116 with respect to the joystick 190 and the dashboard 302 initiates through a homing procedure, which may be done in addition to, simultaneously with, or in place of the homing procedure of the motors. During the homing procedure, the distal tip 116 is automatically moved to the extreme or maximal "up" position followed by the extreme or maximal "down" position and the respective encoder values for these positions are stored in system memory. The same process is done for the extreme or maximal "left" and extreme or maximal "right" positions of the distal tip 116, respectively. These stored encoder values are the maximum and minimum positions of the system in the X and Y axes, respectively. This positional information may be then used to calculate the encoder values for the neutral or home position for the distal tip 116. For the dashboard 302, this neutral/home position is signified by the center of the bounding perimeters 316, 318 or the intersection of the cross-hairs 320, as shown in FIG. 5. Further, the maximum and minimum encoder values for the two axes may be used to give a scaled radius for the bounding perimeters 316, 318. For the dashboard 302, the encoder values may also be scaled to accurately represent them within the oval. Thus, each point within the area of the oval represents a set of encoder values for the two motors which helps determine the location of the distal tip in 2D space (projected from the actual 3D space).

As described above, the system 100 may allow the user to select and move between two or more speeds at which the distal tip 116 moves and/or a responsiveness of the joystick control 190. The dashboard 302 may also be configured to display a selected speed mode, as shown at region 308. For example, the dashboard 302 may illustrate the various speed modes as icons or panels 330, 332. The selected speed mode may be highlighted or illuminated to indicate the selection. In FIG. 5, the normal speed 332 has been selected and is illuminated while the slow speed 330 is shaded. It is contemplated that the selected speed may be highlighted in a same color as the first icon 312 (tip position), although this is not required. Further, while the dashboard 302 is illustrated as including two speeds and two corresponding panels 330, 332, the dashboard 302 may include any number of buttons to correlate to the number of speed options. For example, a "high" speed panel may be provided in addition to or in place of the "slow" panel 330 or "normal" panel 332.

Additionally, the amount of motor torque may also be displayed on the dashboard 302 at the third region 310. The amount of force feedback on the distal tip 116 that the physician would otherwise feel when navigating through the patient's autonomy can be calculated by measuring motor current against motor torque. This may be displayed to the physician as a shaded bar 340 that increases in size with an increase in force. It is contemplated that the shaded bar 340 may be a same color as the first icon 312 (tip position), although this is not required. A maximum torque may extend an entire width of the dashboard 302 or to an identified maximum torque, as desired. Once the shaded bar 340 reaches the maximum force (e.g., the motor torque value at which the motor current reaches the pre-determined permissible limit), the user may be prohibited from increasing the force. This maximum force could be calculated by measuring the motor current against the motor torque through testing. While the torque is illustrated as a shaded bar 340, it is contemplated that the torque may be displayed in other manners as well.

The dashboard 302 may include additional features. For example, the user may have the ability to manipulate the size and location of the dashboard 302 on the screen and the ability to select which dashboard features are displayed at a control bar 350. In some embodiments, the user may choose to display one of or a combination of two or more of: (1) distal tip location 306, (2) speed mode 308, and/or (3) force feedback (e.g., torque) 310. It is further contemplated that the user may selected a display style for any of the (1) distal tip location 306, (2) speed mode 308, and/or (3) force feedback (e.g., torque) 310. For example, alternative display configurations are described below. In some cases, the user can choose to minimize, expand, or close the dashboard 302. Manipulating the dashboard 302 could be accomplished by joystick input, or other input, or by using a touchscreen in order to directly manipulate on the video display screen.

Figure 6:
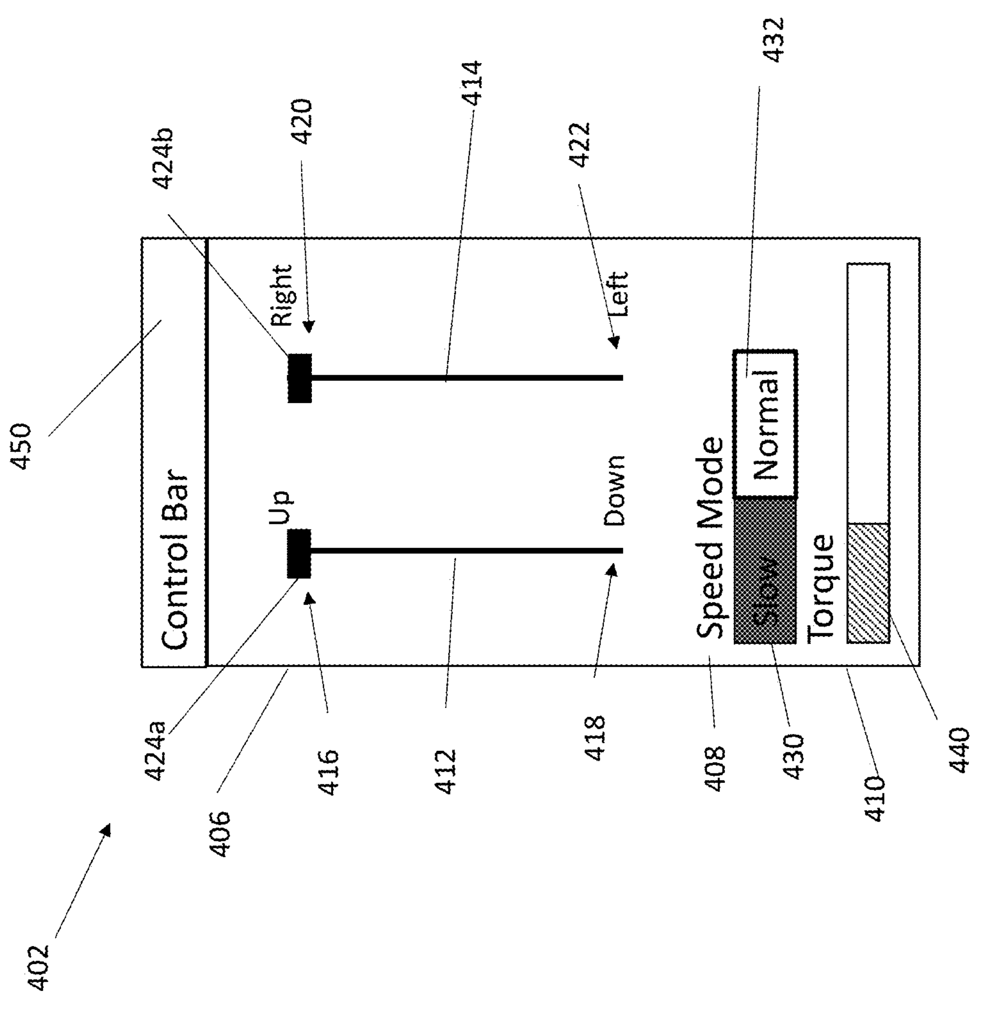

FIG. 6 is a schematic view of an illustrative graphical user interface (GUI) 402 or dashboard for providing feedback to a physician. The dashboard 402 may be displayed, for example, on the touch panel computer 152, or other display device, as desired. The dashboard or window 402 may be visible to the physician and include visual information regarding the distal tip position with respect to the scope, distal tip speed, and an indication of the amount of force exerted on the distal tip 116. In some cases, the distal tip position with respect to the scope may be provided in a first region 406 of the window 402, the distal tip speed provided in a second region 408 of the window, and the indication of the amount of force exerted on the distal tip in a third region 410 of the window 402. In other embodiments, the information may be displayed in more than one window. For example, while not explicitly shown, the first, second, and third regions 406, 408, 410 may each be a separate window. It is further contemplated that the endoscope's camera feed may be displayed in an additional window (not explicitly shown).

In FIG. 6, the location of the distal tip 116 may be represented by vertical sliding toggles 424*a*, 424*b* (collectively, 424). The first sliding toggle 424*a* may move along a first vertical slide bar 412 to illustrate movement (e.g., deflection) of the distal tip 116 in an up/down direction within a first plane. For example, the sliding toggle 424*a* may move anywhere between a lowermost end 418 indicating the distal tip 116 is in the extreme downward deflected configuration and an uppermost end 416 indicating the distal tip 116 is in the extreme upward deflected configuration. The second sliding toggle 424*b* may move along a second vertical slide bar 414 to illustrate movement of the distal tip 116 in a left/right direction in a second plane, which may be perpendicular to the first plane. For example, the sliding toggle 424*b* may move anywhere between a lowermost end 422 indicating the distal tip 116 is in the extreme leftward deflected configuration and an uppermost end 420 indicating the distal tip 116 is in the extreme rightward deflected configuration. When the distal tip 116 is in the neutral position and the joystick 190 is unmoved, both the first and second sliding toggles 424 may be vertically centered along the vertical slide bars 412, 414. As the user jogs or moves the joystick 190 the distal tip 116 moves, and thus the sliding toggles 424. Thus, the amount the sliding toggles 424 move from the center position may represent or correspond to the amount of deflection of the distal tip 116 in the corresponding direction.

While the sliding toggles 424 are illustrated as having a generally rectangular shape, the sliding toggles 424 may take any shape desired, such as, but not limited to, circular, triangular, square, polygonal, etc. Further, the sliding toggles 424 need not have the same shape as one another. In some cases, the sliding toggles 424 may have a color different from the vertical slide bars 412, 414, although this is not required. In some embodiments, the vertical slide bars 412, 414 may include hatch marks or other indicators of intervals between the respective extremes.

When the motorized endoscope system 100 is turned on, the calibration of the distal tip 116 with respect to the joystick 190 and the dashboard 402 initiates through a homing procedure, which may be done in addition to, simultaneously with, or in place of the homing procedure of the motors. During the homing procedure, the distal tip 116 is automatically moved to the extreme or maximal "up" position followed by the extreme or maximal "down" position and the respective encoder values for these positions are stored in system memory. The same process is done for the extreme or maximal "left" and extreme or maximal "right" positions of the distal tip 116, respectively. These stored encoder values are the maximum and minimum positions of the system in the X and Y axes, respectively. This positional information may be then used to calculate the encoder values for the neutral or home position for the distal tip 116. For the dashboard 402, this neutral/home position is signified by the vertical center of the vertical slide bars 412, 414.

Further, the maximum and minimum encoder values for the two axes may be used to give a scaled vertical height for the slide bars 412, 414. For the dashboard 402, the encoder values may also be scaled to accurately represent them along the vertical slide bars 412, 414. Thus, each point along the vertical slide bars represents an encoder value for at least one of the two motors which helps determine the location of the distal tip in 2D space (projected from the actual 3D space).

As described above, the system 100 may allow the user to select and move between two or more speeds at which the distal tip 116 moves and/or a responsiveness of the joystick control 190. The dashboard 402 may also be configured to display a selected speed mode, as shown at region 408. For example, the dashboard 402 may illustrate the various speed modes as icons or panels 430, 432. The selected speed mode may be highlighted or illuminated to indicate the selection. In FIG. 6, the normal speed 432 has been selected and is illuminated while the slow speed 430 is shaded. It is contemplated that the selected speed may be highlighted in a same color as the sliding toggles 424 (tip position), although this is not required. Further, while the dashboard 402 is illustrated as including two speeds and two corresponding panels 430, 432, the dashboard 402 may include any number of buttons to correlate to the number of speed options. For example, a "high" speed panel may be provided in addition to or in place of the "slow" panel 430 or "normal" panel 432.

Additionally, the amount motor torque may also be displayed on the dashboard 402 at the third region 410. The amount of force feedback on the distal tip 116 that the physician would otherwise feel when navigating through the patient's autonomy can be calculated by measuring motor current against motor torque. This may be displayed to the physician as a shaded bar 440 that increases in size with an increase in force. It is contemplated that the shaded bar 440 may be a same color as the sliding toggles 424 (tip position), although this is not required. A maximum torque may extend an entire width of the dashboard 402 or to an identified maximum torque, as desired. Once the shaded bar 440 reaches the maximum force (e.g., the motor torque value at which the motor current reaches the pre-determined permissible limit), the user may be prohibited from increasing the force. This maximum force could be calculated by measuring the motor current against the motor torque through testing. While the torque is illustrated as a shaded bar 440, it is contemplated that the torque may be displayed in other manners as well.

The dashboard 402 may include additional features. For example, the user may have the ability to manipulate the size and location of the dashboard 402 on the screen and the ability to select which dashboard features are displayed at a control bar 450. In some embodiments, the user may choose to display one of or a combination of two or more of: (1) distal tip location 406, (2) speed mode 408, and/or (3) force feedback (e.g., torque) 410. It is further contemplated that the user may selected a display style for any of the (1) distal tip location 406, (2) speed mode 408, and/or (3) force feedback (e.g., torque) 410. For example, alternative display configurations are described below. In some cases, the user can choose to minimize, expand, or close the dashboard 402. Manipulating the dashboard 402 could be accomplished by joystick input, or other input, or by using a touchscreen in order to directly manipulate on the video display screen.

Figure 7:
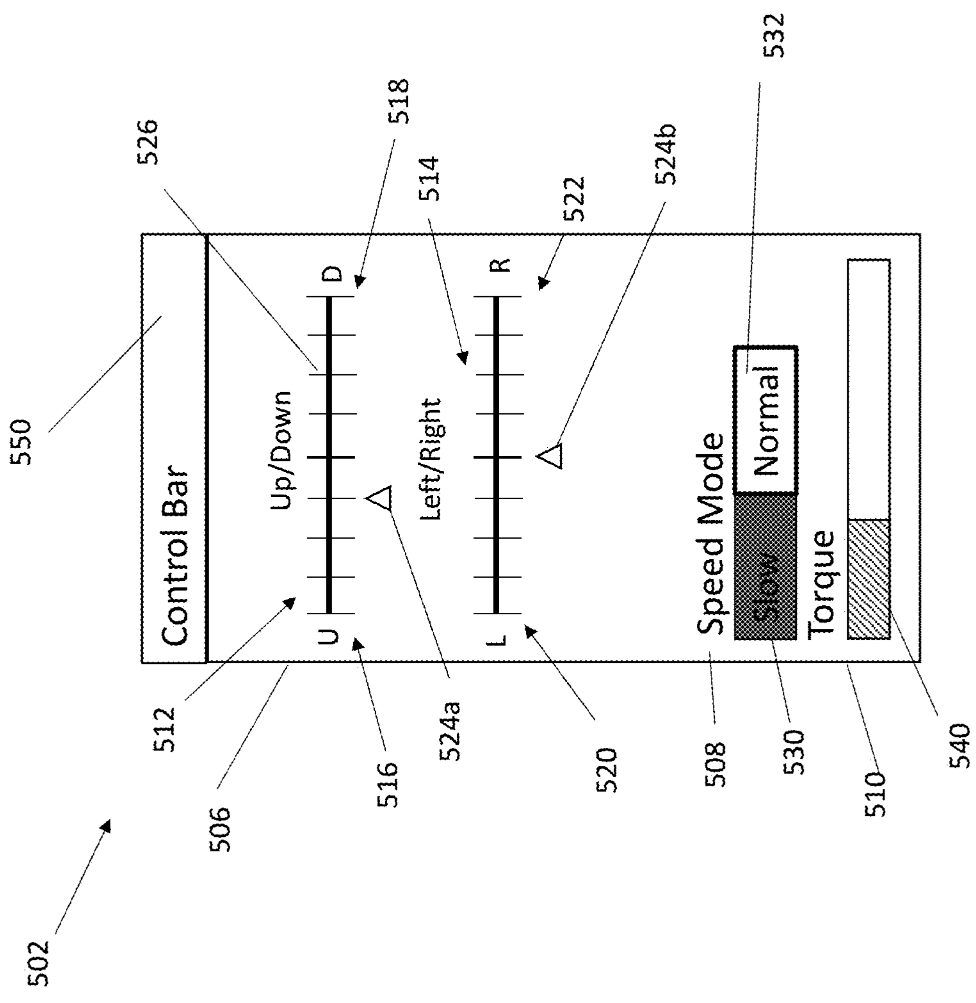

FIG. 7 is a schematic view of an illustrative graphical user interface (GUI) 502 or dashboard for providing feedback to a physician. The dashboard 502 may be displayed, for example, on the touch panel computer 152, or other display device, as desired. The dashboard or window 502 may be visible to the physician and include visual information regarding the distal tip position with respect to the scope, distal tip speed, and an indication of the amount of force exerted on the distal tip 116. In some cases, the distal tip position with respect to the scope may be provided in a first region 506 of the window 502, the distal tip speed provided in a second region 508 of the window, and the indication of the amount of force exerted on the distal tip in a third region 510 of the window 502. In other embodiments, the information may be displayed in more than one window. For example, while not explicitly shown, the first, second, and third regions 506, 508, 510 may each be a separate window. It is further contemplated that the endoscope's camera feed may be displayed in an additional window (not explicitly shown).

In FIG. 7, the location of the distal tip 116 may be represented by horizontal sliding toggles **524*a*, 524*b* (collectively, 524). The first sliding toggle 524*a* may move along a first horizontal slide bar 512 to illustrate movement (e.g., deflection) of the distal tip 116 in an up/down direction within a first plane. For example, the sliding toggle 524*a* may move anywhere between a first end 516 indicating the distal tip 116 is in the extreme upward deflected configuration and a second end 518 indicating the distal tip 116 is in the extreme downward deflected configuration. The second sliding toggle 524*b* may move along a second horizontal slide bar 514 to illustrate movement (e.g., deflection) of the distal tip 116 in a left/right direction within a second plane, which may be perpendicular to the first plane. For example, the sliding toggle 524*b* may move anywhere between a first end 520 indicating the distal tip 116 is in the extreme leftward deflected configuration and a second end 522 indicating the distal tip 116 is in the extreme rightward deflected configuration. When the distal tip 116 is in the neutral position and the joystick 190 is unmoved, both the first and second sliding toggles 524 may be horizontally centered along the horizontal slide bars 512, 514. As the user jogs or moves the joystick 190 the distal tip 116 moves, and thus the sliding toggles 524. Thus, the amount the sliding toggles 524 move from the center position may represent or correspond to the amount of deflection of the distal tip 116** in the corresponding direction.

While the sliding toggles 524 are illustrated as having a generally triangular shape, the sliding toggles 524 may take any shape desired, such as, but not limited to, circular, rectangular, square, polygonal, etc. Further, the sliding toggles 524 need not have the same shape as one another. In some cases, the sliding toggles 524 may have a color different from the horizontal slide bars 512, 514, although this is not required. In some embodiments, the horizontal slide bars 512, 514 may include hatch marks 526 or other indicators of intervals between the respective extremes.

When the motorized endoscope system 100 is turned on, the calibration of the distal tip 116 with respect to the joystick 190 and the dashboard 502 initiates through a homing procedure, which may be done in addition to, simultaneously with, or in place of the homing procedure of the motors. During the homing procedure, the distal tip 116 is automatically moved to the extreme or maximal "up" position followed by the extreme or maximal "down" position and the respective encoder values for these positions are stored in system memory. The same process is done for the extreme or maximal "left" and extreme or maximal "right" positions of the distal tip 116, respectively. These stored encoder values are the maximum and minimum positions of the system in the X and Y axes, respectively. This positional information may be then used to calculate the encoder values for the neutral or home position for the distal tip 116. For the dashboard 502, this neutral/home position is signified by the horizontal center of the horizontal slide bars 512, 514. Further, the maximum and minimum encoder values for the two axes may be used to give a scaled horizontal width for the slide bars 512, 514. For the dashboard 502, the encoder values may also be scaled to accurately represent them along the horizontal slide bars 512, 514. Thus, each point along the horizontal slide bars represents an encoder value for at least one of the two motors which helps determine the location of the distal tip in 2D space (projected from the actual 3D space).

As described above, the system 100 may allow the user to select and move between two or more speeds at which the distal tip 116 moves and/or a responsiveness of the joystick control 190. The dashboard 502 may also be configured to display a selected speed mode, as shown at region 508. For example, the dashboard 502 may illustrate the various speed modes as icons or panels 530, 532. The selected speed mode may be highlighted or illuminated to indicate the selection. In FIG. 7, the normal speed 532 has been selected and is illuminated while the slow speed 530 is shaded. It is contemplated that the selected speed may be highlighted in a same color as the sliding bars 524 (tip position), although this is not required. Further, while the dashboard 502 is illustrated as including two speeds and two corresponding panels 530, 532, the dashboard 502 may include any number of buttons to correlate to the number of speed options. For example, a "high" speed panel may be provided in addition to or in place of the "slow" panel 530 or "normal" panel 532.

Additionally, the amount motor torque may also be displayed on the dashboard 502 at the third region 510. The amount of force feedback on the distal tip 116 that the physician would otherwise feel when navigating through the patient's autonomy can be calculated by measuring motor current against motor torque. This may be displayed to the physician as a shaded bar 540 that increases in size with an increase in force. It is contemplated that the shaded bar 540 may be a same color as the sliding bars 524 (tip position), although this is not required. A maximum torque may extend an entire width of the dashboard 502 or to an identified maximum torque, as desired. Once the shaded bar 540 reaches the maximum force (e.g., the motor torque value at which the motor current reaches the pre-determined permissible limit), the user may be prohibited from increasing the force. This maximum force could be calculated by measuring the motor current against the motor torque through testing. While the torque is illustrated as a shaded bar 540, it is contemplated that the torque may be displayed in other manners as well.

The dashboard 502 may include additional features. For example, the user may have the ability to manipulate the size and location of the dashboard 502 on the screen and the ability to select which dashboard features are displayed at a control bar 550. In some embodiments, the user may choose to display one of or a combination of two or more of: (1) distal tip location 506, (2) speed mode 508, and/or (3) force feedback (e.g., torque) 510. It is further contemplated that the user may selected a display style for any of the (1) distal tip location 506, (2) speed mode 508, and/or (3) force feedback (e.g., torque) 510. For example, alternative display configurations are described below. In some cases, the user can choose to minimize, expand, or close the dashboard 502. Manipulating the dashboard 502 could be accomplished by joystick input, or other input, or by using a touchscreen in order to directly manipulate on the video display screen.

Figure 8:
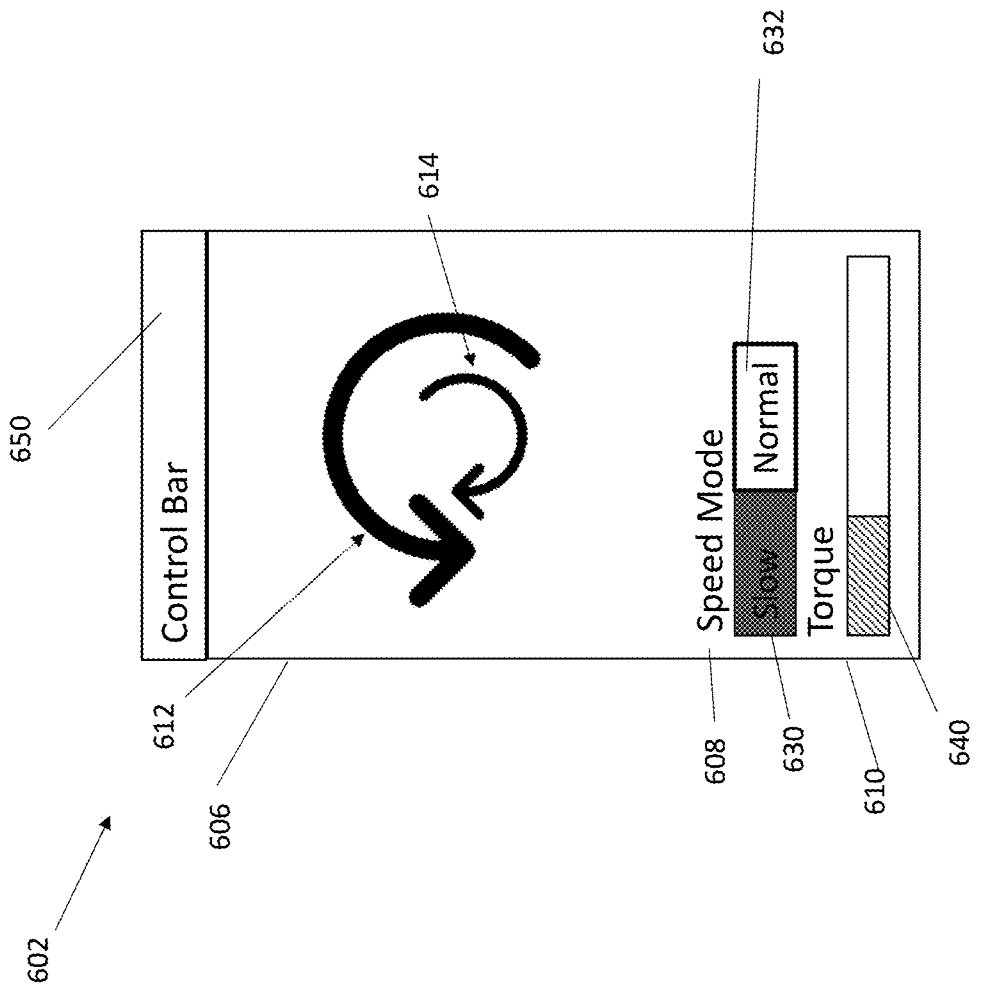

FIG. 8 is a schematic view of an illustrative graphical user interface (GUI) 602 or dashboard for providing feedback to a physician. The dashboard 602 may be displayed, for example, on the touch panel computer 152, or other display device, as desired. The dashboard or window 602 may be visible to the physician and include visual information regarding the distal tip position with respect to the scope, distal tip speed, and an indication of the amount of force exerted on the distal tip 116. In some cases, the distal tip position with respect to the scope may be provided in a first region 606 of the window 602, the distal tip speed provided in a second region 608 of the window, and the indication of the amount of force exerted on the distal tip in a third region 610 of the window 602. In other embodiments, the information may be displayed in more than one window. For example, while not explicitly shown, the first, second, and third regions 606, 608, 610 may each be a separate window. It is further contemplated that the endoscope's camera feed may be displayed in an additional window (not explicitly shown).

In FIG. 8, the location of the distal tip 116 may be represented by a first arc 612 and a second arc 614. For example, a first arc 612 may represent up/down movement (e.g., deflection) of the distal tip 116 in a first plane and a second arc 614 may represent left/right movement (e.g., deflection) of the distal tip 116 in a second plane, which may be perpendicular to the first plane. The arcs 612, 614 may be reminiscent of the dials on a traditional (e.g., non-motorized) endoscope so as to be familiar to the user. Accordingly, the length of the first arc 612 may represent or correspond to the amount of deflection of the distal tip 116 in the up/down direction in the first plane and the length of the arc 614 may represent or correspond to the amount of deflection of the distal tip 116 in the left/right direction within the second plane. It is contemplated that directional information (such as that displayed on the sliders in FIGS. 6 and 7) may be used to transform the directional information into the arcs 612, 614. For example, polar coordinates may be used to transform linear information into an arc of a dial and/or circle.

In some examples, the arcs 612, 614 may include a marker or other visual indicia displayed proximate thereto that is indicative of a relative position of the distal tip 116. For example, the first arc 612 may include nearby markers for the upmost (extreme up) position, the neutral position, and the downmost (extreme down) position of the distal tip 116. Similarly, the second arc 614 may include nearby markers for the leftmost (extreme left) position, the neutral position, and the rightmost (extreme right) position of the distal tip 116. Additional position markers may be provided, as desired. It is contemplated that the markers may be formed from different colors, sizes, shapes, etc. to differentiate the neutral positions from the extreme positions. In one example, the neutral position for the first and second arc 612, 614 may be identified with a first color and the extreme positions (up, down, left, right) identified with one or more colors different from the first color. In another example, letters may be used to identify the makers. For example, "N" could be used to identify the neutral position marker, "U" could be used to identify the upmost marker, "D" could be used to identify the downmost marker, "L" could be used to identify the leftmost marker, and "R" could be used to identify the rightmost marker. These are just some examples. Other identifying marks or visual indicia may be used as desired.

When the motorized endoscope system 100 is turned on, the calibration of the distal tip 116 with respect to the joystick 190 and the dashboard 602 initiates through a homing procedure, which may be done in addition to, simultaneously with, or in place of the homing procedure of the motors. During the homing procedure, the distal tip 116 is automatically moved to the extreme or maximal "up" position followed by the extreme or maximal "down" position and the respective encoder values for these positions are stored in system memory. The same process is done for the extreme or maximal "left" and extreme or maximal "right" positions of the distal tip 116, respectively. These stored encoder values are the maximum and minimum positions of the system in the X and Y axes, respectively. This positional information may be then used to calculate the encoder values for the neutral or home position for the distal tip 116.

As described above, the system 100 may allow the user to select and move between two or more speeds at which the distal tip 116 moves and/or a responsiveness of the joystick control 190. The dashboard 602 may also be configured to display a selected speed mode, as shown at region 608. For example, the dashboard 602 may illustrate the various speed modes as icons or panels 630, 632. The selected speed mode may be highlighted or illuminated to indicate the selection. In FIG. 8, the normal speed 632 has been selected and is illuminated while the slow speed 630 is shaded. Further, while the dashboard 602 is illustrated as including two speeds and two corresponding panels 630, 632, the dashboard 602 may include any number of buttons to correlate to the number of speed options. For example, a "high" speed panel may be provided in addition to or in place of the "slow" panel 630 or "normal" panel 632.

Additionally, the amount motor torque may also be displayed on the dashboard 602 at the third region 610. The amount of force feedback on the distal tip 116 that the physician would otherwise feel when navigating through the patient's autonomy can be calculated by measuring motor current against motor torque. This may be displayed to the physician as a shaded bar 640 that increases in size with an increase in force. A maximum torque may extend an entire width of the dashboard 602 or to an identified maximum torque, as desired. Once the shaded bar 640 reaches the maximum force (e.g., the motor torque value at which the motor current reaches the pre-determined permissible limit), the user may be prohibited from increasing the force. This maximum force could be calculated by measuring the motor current against the motor torque through testing. While the torque is illustrated as a shaded bar 640, it is contemplated that the torque may be displayed in other manners as well.

The dashboard 602 may include additional features. For example, the user may have the ability to manipulate the size and location of the dashboard 602 on the screen and the ability to select which dashboard features are displayed at a control bar 650. In some embodiments, the user may choose to display one of or a combination of two or more of: (1) distal tip location 606, (2) speed mode 608, and/or (3) force feedback (e.g., torque) 610. It is further contemplated that the user may selected a display style for any of the (1) distal tip location 606, (2) speed mode 608, and/or (3) force feedback (e.g., torque) 610. For example, alternative display configurations are described below. In some cases, the user can choose to minimize, expand, or close the dashboard 602. Manipulating the dashboard 602 could be accomplished by joystick input, or other input, or by using a touchscreen in order to directly manipulate on the video display screen.

In some embodiments, the endoscope(s), the motor control assembly (assemblies), and/or the controller described herein may include one or more safety mechanisms configured to prevent tissue damage and/or damage to the endoscope itself. In some embodiments, the endoscope(s) may include on/off indicators (e.g., lights, LEDs, etc.) showing the user whether or not selected features are engaged or disabled. In some embodiments, a strain gauge on the cable, wire, or filament engaged with the pulley, or optical strain gauge fibers, may be used to infer pressure exerted by the endoscope on adjacent tissue. In any case, a safety threshold for pressure or strain may be an adjustable input variable that the user is able to choose and/or adjust before and/or during the procedure. When the pressure or strain exceeds the safety threshold, the distal tip may return to the home position, or other pre-programmed actions may be implemented. In some embodiments, the user may choose between these options as another user input factor. In some embodiments, there may be more than one pressure or strain safety threshold. In some embodiments, the safety threshold(s) may be activated and/or deactivated by users via voice commands, buttons on the endoscope, touchscreen controls, or other methods.

The materials that can be used for the various components of the system(s) and the various elements thereof disclosed herein may include those commonly associated with medical devices. For simplicity purposes, the following discussion refers to the system. However, this is not intended to limit the devices and methods described herein, as the discussion may be applied to other elements, members, components, or devices disclosed herein, such as, but not limited to, the handle(s), the elongate shaft(s), the deflection mechanism(s), the motor(s), the pulley(s), the drive axle(s), the joystick control(s), the button(s), the distal tip(s), the motor control housing(s), etc., and/or elements or components thereof.

In some embodiments, the system, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the system, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MRI) compatibility is imparted into the system and/or other elements disclosed herein. For example, the system, and/or components or portions thereof, may be made of a material that does not substantially distort the image and create substantial artifacts (i.e., gaps in the image). Certain ferromagnetic materials, for example, may not be suitable because they may create artifacts in an MRI image. The system, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the present disclosure. This may include, to the extent that it is appropriate, the use of any of the features of one example embodiment being used in other embodiments. The scope of the present disclosure is, of course, defined in the language in which the appended claims are expressed.

What is claimed is:

1. A steerable medical device and display system, comprising:

- a handle and an elongate shaft extending distally from the handle to a distal tip;
- a motor control assembly including a motor control housing configured to detachably interface with the handle;
- a first deflection mechanism disposed within the handle, the first deflection mechanism being configured to deflect the distal tip in a first plane;
- a motorized control interface configured to operate at least one motor disposed within the motor control housing; and
- a work station in electronic communication with the motor control assembly, the work station including at least a display screen;
- wherein the work station is configured to display a dashboard including visual information of a position of the distal tip;
- wherein the visual information includes a first bounding perimeter representing an available range of movement of the distal tip and a second bounding perimeter representing an available range of movement of the motorized control interface;
- wherein the first bounding perimeter and the second bounding perimeter are concentric circles.

2. The system of claim 1, wherein the visual information includes a location of the distal tip in two dimensions.

3. The system of claim 1, wherein the motorized control interface includes a joystick control configured to operate the at least one motor to drive the first deflection mechanism.

4. The system of claim 3, wherein the visual information includes a location of the joystick control in two dimensions.

5. The system of claim 1, wherein the visual information includes a speed mode.

6. The system of claim 1, wherein the visual information includes an indication of motor torque.

7. A steerable medical device and display system, comprising:

a handle and an elongate shaft extending distally from the handle to a distal tip;

a motor control assembly including a motor control housing configured to detachably interface with the handle;

a first deflection mechanism disposed within the handle, the first deflection mechanism being configured to deflect the distal tip in a first plane;

a motorized control interface configured to operate at least one motor disposed within the motor control housing; and a work station in electronic communication with the motor control assembly, the work station including at least a display screen;

wherein the work station is configured to display a dashboard including visual information of a position of the distal tip and a position of the motorized control interface;

wherein the visual information includes a first bounding perimeter representing an available range of movement of the distal tip and a second bounding perimeter representing an available range of movement of the motorized control interface;

wherein the first bounding perimeter and the second bounding perimeter are concentric circles.

8. The system of claim 7, wherein the position of the distal tip is represented by a first icon and the position of the motorized control interface is represented by a second icon.

9. The system of claim 8, wherein the first icon is configured to move on the display in response to movement of the distal tip.

10. The system of claim 8, wherein the second icon is configured to move on the display in response to movement of the motorized control interface.

11. The system of claim 7, wherein a center point of the first and second bounding perimeters are a neutral position for the distal tip and the motorized control interface.

12. A steerable medical device and display system, comprising:

a handle and an elongate shaft extending distally from the handle to a distal tip;

a motor control assembly including a motor control housing configured to detachably interface with the handle;

a first deflection mechanism disposed within the handle, the first deflection mechanism being configured to deflect the distal tip in a first plane;

a motorized control interface configured to operate at least one motor disposed within the motor control housing; and a work station in electronic communication with the motor control assembly, the work station including at least a display screen;

wherein the work station is configured to display a dashboard including visual information of a position of the distal tip, a position of the motorized control interface, a selected speed mode and/or a motor torque;

wherein the visual information includes a first bounding perimeter representing an available range of movement of the distal tip and a second bounding perimeter representing an available range of movement of the motorized control interface;

wherein the first bounding perimeter and the second bounding perimeter are concentric circles.

13. The system of claim 1, wherein the position of the distal tip is represented by a first icon and the position of the motorized control interface is represented by a second icon.

14. The system of claim 13, wherein the first icon is configured to move on the display in response to movement of the distal tip.

15. The system of claim 13, wherein the second icon is configured to move on the display in response to movement of the motorized control interface.

16. The system of claim 1, wherein the position of the distal tip is represented by a first icon and the position of the motorized control interface is represented by a second icon.

17. The system of claim 16, wherein the first icon is configured to move on the display in response to movement of the distal tip.

18. The system of claim 16, wherein the second icon is configured to move on the display in response to movement of the motorized control interface.

* * * * *